(12) United States Patent
Ueda

(10) Patent No.: US 10,494,606 B2
(45) Date of Patent: Dec. 3, 2019

(54) IMMORTALIZED STEM CELL, COMPOSITIONS, PREPARATIONS AND USES THEREOF

(71) Applicant: Quarrymen & Co. Inc., Tokyo (JP)

(72) Inventor: Minoru Ueda, Tokyo (JP)

(73) Assignee: QUARRYMEN&Co. Inc., Tokyo (JP)

(*) Notice: Subject to any disclaimer, the term of this patent is extended or adjusted under 35 U.S.C. 154(b) by 0 days.

(21) Appl. No.: 15/632,831

(22) Filed: Jun. 26, 2017

(65) Prior Publication Data

US 2017/0355960 A1 Dec. 14, 2017

Related U.S. Application Data

(60) Division of application No. 14/499,171, filed on Sep. 27, 2014, now abandoned, which is a continuation-in-part of application No. PCT/JP2013/059376, filed on Mar. 28, 2013.

(30) Foreign Application Priority Data

| Mar. 28, 2012 | (JP) | 2012-073594 |
| Aug. 28, 2012 | (JP) | 2012-187321 |
| Dec. 17, 2012 | (JP) | 2012-275169 |
| Feb. 14, 2013 | (JP) | 2013-026886 |

(51) Int. Cl.

| C12N 5/00 | (2006.01) |
| C12N 5/0775 | (2010.01) |
| C12N 5/074 | (2010.01) |
| A61K 38/18 | (2006.01) |
| A61K 38/30 | (2006.01) |
| A61K 35/28 | (2015.01) |
| A61K 35/32 | (2015.01) |
| A61K 35/54 | (2015.01) |
| A61K 9/00 | (2006.01) |
| C12N 15/85 | (2006.01) |

(52) U.S. Cl.
CPC .......... *C12N 5/0664* (2013.01); *A61K 9/0014* (2013.01); *A61K 9/0043* (2013.01); *A61K 35/28* (2013.01); *A61K 35/32* (2013.01); *A61K 35/54* (2013.01); *A61K 38/1833* (2013.01); *A61K 38/1841* (2013.01); *A61K 38/1866* (2013.01); *A61K 38/30* (2013.01); *C12N 5/0696* (2013.01); *C12N 15/85* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2506/1346* (2013.01); *C12N 2506/1361* (2013.01)

(58) Field of Classification Search
None
See application file for complete search history.

(56) References Cited

U.S. PATENT DOCUMENTS

2013/0195991 A1* 8/2013 Ueda .................... A61K 35/545
424/572

FOREIGN PATENT DOCUMENTS

| EP | 2 096 169 A1 | 9/2009 |
| JP | 2004-000497 A | 1/2004 |
| JP | 2010-046019 A | 3/2010 |
| JP | 2011-212023 A | 10/2011 |
| JP | 4831687 B2 | 12/2011 |
| JP | 2013-018756 A | 1/2013 |
| WO | WO-2006/009291 A1 | 1/2006 |
| WO | WO-2010/013845 A1 | 2/2010 |
| WO | WO-2010/033088 A2 | 3/2010 |
| WO | WO-2010/105257 A2 | 9/2010 |
| WO | WO-2010/105311 A1 | 9/2010 |
| WO | WO-2011/118795 A1 | 9/2011 |

OTHER PUBLICATIONS

Mori et al. (2005) "Combination of hTERT and bmi-1, E6, or E7 Induces Prolongation of the Life Span of Bone Marrow Stromal Cells from an Elderly Donor without Affecting Their Neurogenic Potential," Molecular and Cellular Biology, 25: 5183-5195.
Yang et al. (2007) "STRO-1 Selected Rat Dental Pulp Stem Cells Transfected with Adenoviral-Mediated Human Bone Morphogenetic Protein 2 Gene Show Enhanced Odontogenic Differentiation," Tissue Engineering, 13: 2803-281.

(Continued)

*Primary Examiner* — Maria G Leavitt
(74) *Attorney, Agent, or Firm* — Locke Lord LLP; James E. Armstrong, IV; Andrew W. Smith

(57) ABSTRACT

The purpose of the present invention is to provide immortalized stem cells, which produce a growth factor capable of regenerating various kinds of tissues that have been damaged by a variety of causes, and a method for producing the aforesaid immortalized stem cells. Another purpose is to provide a medicinal composition and a medicinal preparation for restoring damaged tissues, and a method for the percutaneous absorption of a culture supernatant. Provided are immortalized stem cells that are obtained by isolating stem cells selected from the group consisting of mammalian mesenchymal cells, an embryo at the early stage of the development and somatic cells, first culturing the cells to give first stage culture cells, transferring four kinds of genes into the first stage culture cells to give transgenic cells, and selecting the desired immortalized stem cells from among the transgenic cells using the expression of STRO-1 as an index.

3 Claims, 17 Drawing Sheets

(11 of 17 Drawing Sheet(s) Filed in Color)

(56) References Cited

OTHER PUBLICATIONS

Yang et al. (2007) "Multilineage potential of STRO-$_{1+}$rat dental pulp cells in vitro," Journal of Tissue Engineering and Regenerative Medicine, 1:128-135.
Yang et al., (2009) "Hard Tissue Formation of STRO-$_1$-Selected Rat Dental Pulp Stem Cells in Vivo," Tissue Engineering, 15:367-377.
Varnum-Finney et al "Pluripotent, cytokine-dependent, hematopoietic stem cells are immortalized by constitutive Notch1 signaling," Nature Medicine 6, 1278-1281 (2000).
Miura et al "SHED: Stem cells from human exfoliated deciduous teeth," PNAS pp. 5807-5812.
Swanson et al "Fertilization and Mouse Embryo Development in the Presence of Midazolam," Anesth Analg 1992;75: 549-54.
K. Okita et al., "Generation of germline-competent induced pluripotent stem cells," Nature. vol. 448: 313-317 (2007).
IPOS Written Opinion, Application No. 11201406141U, dated Oct. 23, 2015.
Extended European Search Report, Application No. 13769656.3, dated Aug. 3, 2015.
Osafune et al "Marked differences in differentiation propensity among human embryonic stem cell lines," Nature Biotechnology vol. 26 No. 3 Mar. 2008 pp. 313-315.
Tomokazu Hasegawa, "Investigation of New Strategy for Periodontal Tissue Regeneration Using with Human Immortalized Periodontal Ligament Cell Line Derived from Deciduous Teeth," Japanese Journal of Pediatric Dentistry, 2012, vol. 50 (1), pp. 7-14.
Simon et al "The role of oxygen availability in embryonic development and stem cell function," Review Nature Reviews Molecular Cell Biology 9, 285-296 (Apr. 2008).
Wang et al "Hypoxia Promotes Dopaminergic Differentiation of Mesenchymal Stem Cells and Shows Benefits for Transplantation in a Rat Model of Parkinson's Disease," PLOS One Jan. 2013 | vol. 8 | Issue 1 | e54296 e54296.
Iohara et al "A Novel Stem Cell Source for Vasculogenesis in lschemia: Subfraction of Side Population Cells from Dental Pulp Stem Cells," vol. 26, Issue 9 Sep. 2008 pp. 2408-2418.

* cited by examiner

Fig. 3
(A)
(B)

Fig. 6
(A)
(B)

Fig. 8
(A)          8 (B)
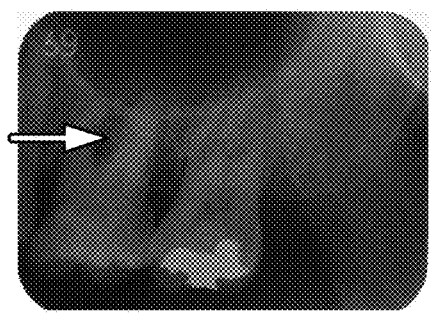 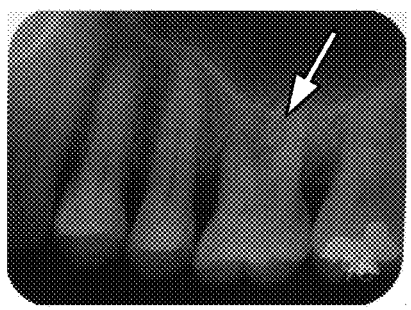
Fig. 9
(A)          (B)
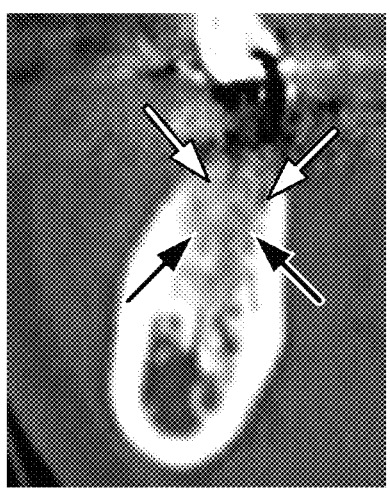 

Fig.11 Transnasal administration of stem cell based growth factors through olfactorius Fig. 15
(A)
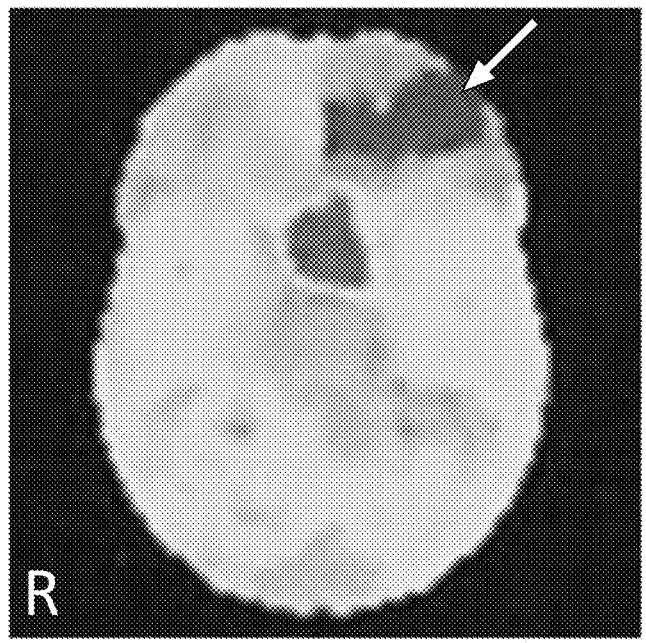
(B)
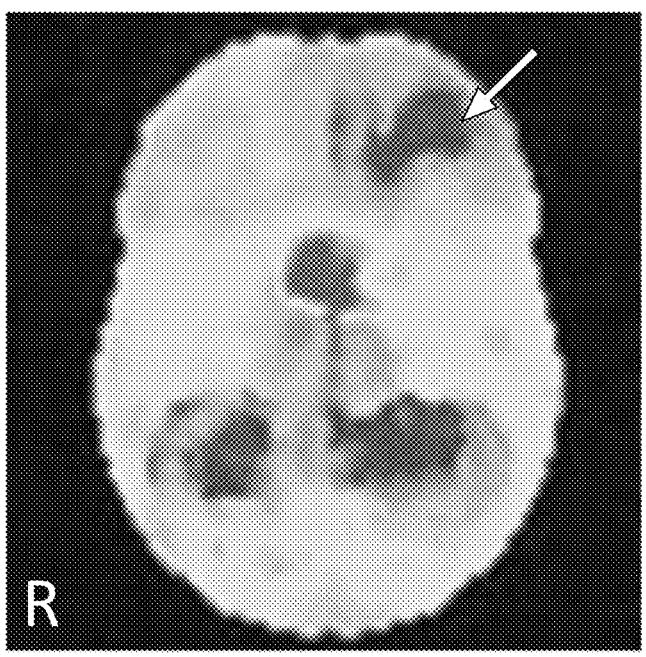

Fig. 17
Fig. 17(A)
Fig. 17(B)

Fig. 18
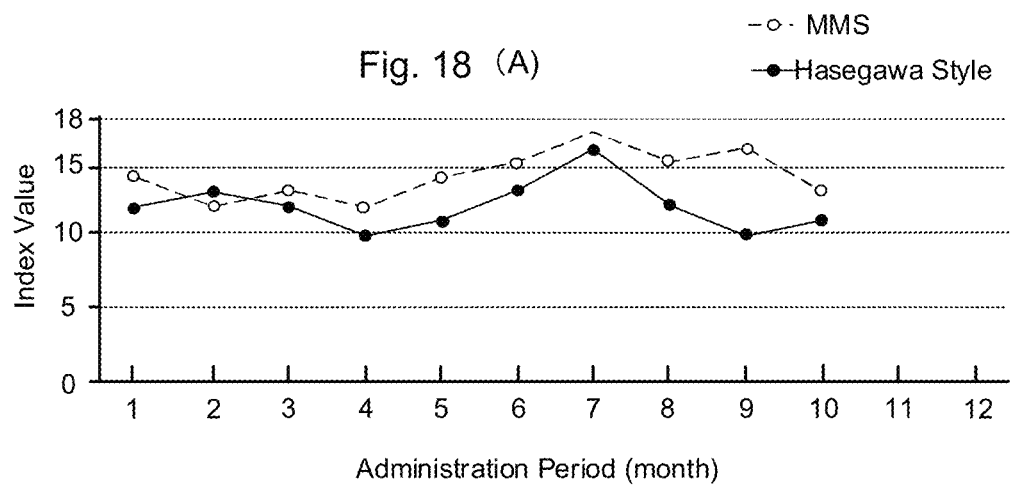
Fig. 18 (A)
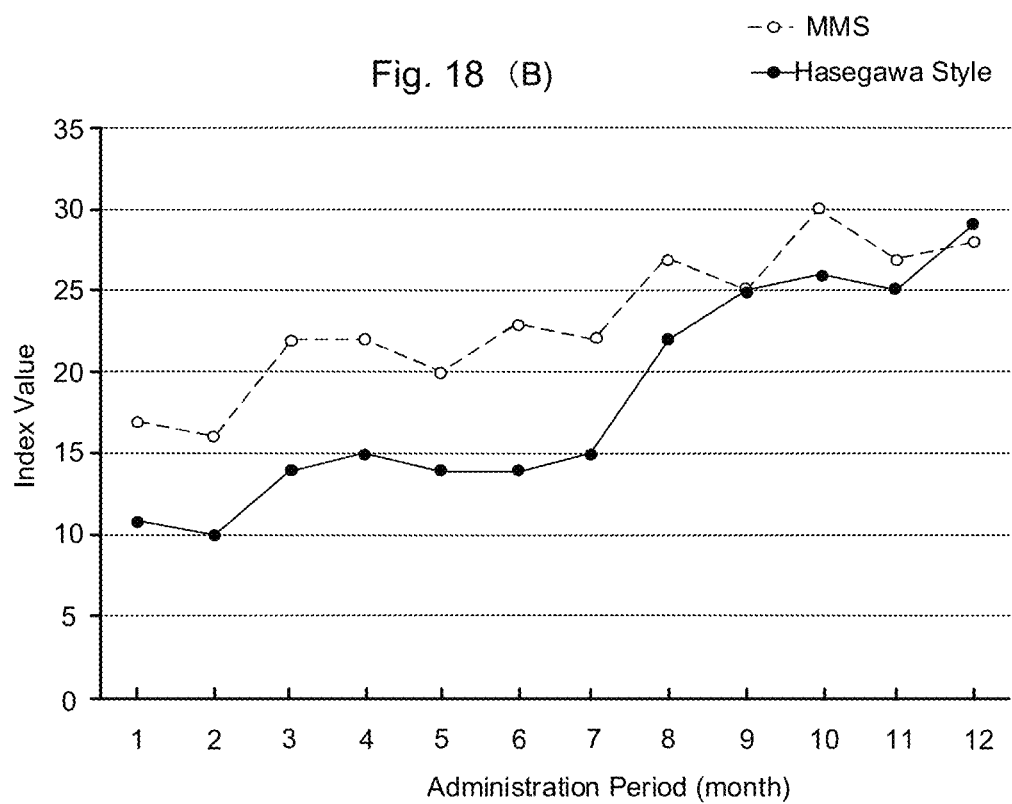
Fig. 18 (B)

Fig. 19
(A)    (B) 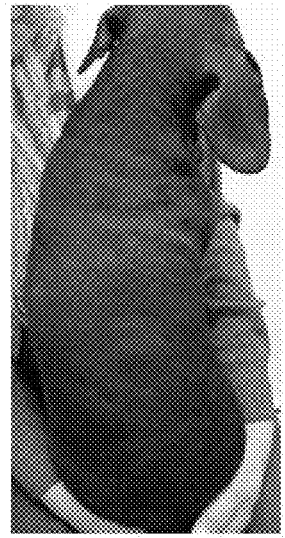

IMMORTALIZED STEM CELL, COMPOSITIONS, PREPARATIONS AND USES THEREOF

This application is a Division of application of U.S. Ser. No. 14/499,171 filed on Sep. 27, 2014, now abandoned. Application Ser. No. 14/499,171 is a Continuation-in-part of Application PCT/JP2013/059376 filed on Mar. 28, 2013, which claims the right of priority under 35 U.S.C. § 119 based on Japanese Patent Application Nos. 2013-026886 filed on Feb. 14, 2013; 2012-275169 filed on Dec. 17, 2012, 2012-187321 filed on Aug. 28, 2012 and 2012-073594 filed on Mar. 28, 2012. The entire contents of these applications are incorporated herein by reference in their entirety.

TECHNICAL FIELD

The present invention relates to an immortalized stem cell derived from a dental pulp, and a composition, particularly a pharmaceutical composition and a preparation, particularly a pharmaceutical preparation both comprising thereof as an active ingredient. Specifically, it relates to the immortalized stem cell which is produced by modifying the stem cell obtained from the naturally exfoliated or removed human dens deciduous or human dens permanence, the composition (e.g., pharmaceutical composition) comprising a variety of growth factors produced by the immortalized cell, and the preparation (e.g., pharmaceutical preparation) comprising thereof. Also provided are methods of using said compositions and preparations for repairing damaged tissue.

BACKGROUND ART

Methods for recovering functions of a damaged tissue caused by a variety of reasons are roughly classified as transplant therapy and regeneration therapy. In transplant therapy, organs provided from a donor are transplanted to replace a recipient's organs to restore lost functions of a living body.

In contrast, in regeneration therapy cells or tissues from several persons including the patient are cultured to be processed to form the organs. These cells replace those with injuries to repair or regenerate them by using the stem cells.

At present, three types of cells such as a human somatic stem cell, a human embryonic stem cell (ES cell), and human induced pluripotent stem cell (iPS cell) are applied or said that they are applicable to the regeneration therapy.

Here, the human somatic stem cell has been already used in a study. It exists in adult tissues and can only differentiate into specified tissue, or organs. Note that "mesenchymal cell" existing in a bone marrow or adipose cells can unusually be differentiated into a variety of tissues such as a bone, a cartilage, an artery and vein. When such somatic cells are used, use of autologous cell prevents immune rejection, and gives good engraftment. Furthermore, there is no report that long term cultivation of these stem cell results in transforming them into tumor cells.

On the other hand, it is known that cells to be differentiated are limited to some extent, the cell collection from the human tissue accompanies invasion, the tissue types to be formed by the differentiated cells are limited in some extent, and capable passage number are limited to forty and several times, namely, 100 to 200 days being calculated in terms of day numbers.

A human embryonic stem cell (ES cell) is the stem cell which is derived from the "inner cell mass" in surplus embryo (blastocyst) obtained from regeneration therapy and the like to be cultured. Since it forms teratoma as an index for its pluripotency, it may be differentiated into any one of the tridermic phases. There is a report that it could be differentiated into myocardium, nerve, and retina. Since the embryonic stem cell (ES) is an immortalized cell strain, one strain among them is continuously cultured endlessly. Then, under the proper culture conditions, a product may have stable properties as the cell is manufactured on a large scale.

On the other hand, it utilizes a fertilized ovum so that it requires strict handling not so as to cause ethical problems. Also, they are basically hetero-transplantation; it requires means to prevent a rejection response by an immune response. Further, it is known that they requires heterologous cell or serum, when the cells ae cultured; and they easily form the teratoma (benign tumor), if the very few number of undifferentiated cells are mixed in a transplanted regenerated tissue.

Human induced pluripotent stem (iPS) cell is established by introducing a part of genes, which are specifically expressed in the ES cell into a human adult cell (dermis and the like). If autologous iPS cells are used, the immune rejection problem does not occur; the differentiation technique is employed for ES cell as is. Finally, the induced pluripotent stem (iPS) cell does not use the fertilized ovum which is used in ES cells, but uses an adult tissue to enable to produce a cell having the same quality as that of the embryonic stem cell. There is no problem of the rejection response by the immune response when the autologous iPS cell is utilized.

On the other hand, it is known that the iPS cells are easily turned into benign tumor cells or cancer cells (embryo cell tumor) and the ratio of the cells established as iPS cells is low; because the morphologically similar cells to ES cells are selected from the whole cells to which genes are introduced.

The use of the stem cell itself in the regeneration therapy has the problems described above. Therefore, a method for using biological factors produced by the various stem cells, not but using the stem cells by themselves, for example, a variety of growth factors are disclosed (WO 2011/118795, herein below, it is referred to as a "prior art 1"). In particular, the prior art 1 (WO 2011/118795) discloses a composition for treating the damaged area comprising a culture sup of the stem cell derived from such as human exfoliated dens deciduous and the like, namely the culture sup including the growth factors such as vein epithelial cell growth factor (VEGF), hepatocyte growth factor (HGF), insulin-like growth factor (IGF), platelet-derived growth factor (PDGF), transformation growth factor-$\beta$ (TGF-$\beta$) and the like.

However, since the stem cell derived from the dental pulp used is not an established cell line, the culture sup of the stem cell of the interest cannot be obtained, unless the stem cell is prepared at a time of use, or a cryopreserved sample is melted to grow the cells. Therefore, there is the problem that it takes time to obtain the culture sup.

In general, among the cultured cells, the cell strain established from a normal cell cannot divide after 50 to 60 times of passage, and the cell dies. Naturally, ratios in the composition of the biological factors produced by the cultivated cells are changing in a time-dependent manner. Therefore, there is the difficult problem to obtain the culture supernatant having stable ratios of them, if the lined cells being capable of unlimited growth.

On the other hand, a typical cell being capable of unlimited growth is a cancer cell. This is caused by the cancer cell which is out of control to grow unlimitedly, although such growth and division of the normal cell is under control of the living body. Therefore, even if the cell may grow unlimitedly, such cancer cells will not be of any use, because the cells may produce biological factors harmful for the living body.

As described above, there is a strong need to establish the immortalized cell which is not cancerous, but grow unlimitedly.

In order to use the supernatant as the pharmaceutical preparation, the immortal stem cell would be able to continuously produce the certain biological factors.

SUMMARY

The first aspect of the present invention is an isolated immortalized stem cell, isolated from a stem cell selected from the group consisting of non-mesenchymal mammalian somatic cell, early-developed embryo and mesenchymal stem cell, which as will be set forth in further detail below is isolated by performing a primary culture of said stem cell; transfecting 4 genes into said primarily cultured stem cell to create a gene transfected cell; selecting said immortalized stem cell, wherein said stem cell expresses STRO-1 and isolating said selected immortalized stem cell. Said mammal is preferably selected from the group consisting of human, swine, equine and monkey.

Said early-developed embryo is preferably the blastoderm of an embryo. Here, said mesenchymal stem cell is preferably selected from the group consisting of dental pulp stem cell, bone marrow stem cell, umbilical stem cell, and adipose stem cell. Furthermore, said stem cell is preferably selected from the group consisting of exfoliated dens deciduous, exfoliated dens permanence, removed dens deciduous, and removed dens permanence.

Said bone marrow stem cell is preferably the cell having with differentiation, ability to become the mesenchymal system such as osteoblast cell to generate the bone, the cartilage, the adipocyte and the like, and non-mesenchymal system. Said umbilical cord cell is the hematopoietic stem cells and the mesenchymal cell included in the umbilical blood that connects the embryo and a placenta. Preferably, the umbilical cord cell includes many of these cells. Said bone marrow stem cell is preferably the cell having with differentiation, ability to become the mesenchymal system such as an osteoblast cell to generate the bone, the cartilage, the adipocyte and the like, and non-mesenchymal system. The umbilical cord cell is preferably obtained from Warton's jelly. The adipocyte stem cell is preferably undifferentiated cell which may differentiate any stem cells.

Said 4 genes are preferably selected from the group consisting of hTERT gene, bmi-1 gene, E6 gene, E7 gene, Oct3/4 gene, Sox2 gene, Klf4 gene, c-Myc gene and p16INK4a gene. Here, they are preferably hTERT, bmi-1, E6 and E7 for being introduced into the mesenchymal cell. Also, they are preferably 4 genes selected from the group consisting of Oct3/4, Sox2, Klf4, c-Myc, p16INK4a for being introduced into the somatic cell.

Said immortalized stem cell preferably has a telomere repairing ability and has an ability to divide at least 200 times. Also, at least 40% of cell population derived from said immortalized stem cell have population doubling time of at least 20. Further, said immortalized stem cell has neonatal bone mass production ability at least equal to those of a primary cultured cell.

Furthermore, said immortalized stem cell preferably secretes at least IGF-1, VEGF, TGF-β1 and HGF into said culture sup.

The second aspect of the present invention is a composition (e.g., pharmaceutical composition) comprising said culture sup of said immortalized stem cell having the properties as mentioned above.

Also, the third aspect of the present invention is a preparation (e.g., pharmaceutical preparation) for restoring damaged tissue comprising said pharmaceutical composition. Here, the dosage forms of the pharmaceutical preparation or composition is in dosage forms selected from the group consisting of powder, liquid, gel, spray and percutaneous system. Also, said damaged tissue is preferably any one of tissue selected from the group consisting of a damaged tissue with ulcer or bedsore, a damaged brain issue by cell degeneration, a brain tissue partially lost by a surgical operation, brain tissue damaged by traumatic brain disease, a damaged brain tissue with inflammatory brain disease, a damaged bone tissue, a damaged periodontal tissue, a damaged tissue by a central neuro system disease, and a damaged tissue by refractory skin disease.

Here, said cell degeneration is preferably caused by the disease selected from the group consisting of Alzheimer disease, Parkinson's disease, cognitive impairment, schizophrenia, depression disease, cerebral hypoxia, amyotrophic lateral sclerosis, cerebral infarction, cerebellar degeneration, diabetes, and hepatitis. Also, said traumatic brain disease is preferably caused by a traffic accident or fall accident. Said inflammatory encephalopathy is also preferably a disease selected from the group consisting of encephalitis encephalopathy, epileptic, Jakob disease, and polio. Furthermore, said central nervous system disease is preferably selected from the group consisting of spinal cord injury and myelopathy. Said refractory dermatitis is preferably atopic dermatitis.

Further, the content of the culture sup of the composition or preparation is preferably 50 to 500% (w/v) when the sup produced by the any one of the immortalized stem cell is 100% of that of the original culture sup.

In a related aspect is a method of using said composition or preparations for the specific purposes set forth above, including but not limited to restoring damaged tissue by administering said composition or preparation to a subject in need thereof in an amount effective to restore damaged tissue.

The fourth aspect of the present invention is a method for producing an immortalized stem cell comprising the steps of: separating a stem cell from cell population selected from the group consisting of mammalian mesenchymal cell, early-developed embryo and a somatic cell other than said mesenchymal cell; culturing said stem cell as primary culture to obtain a primarily cultured cell; transfecting 4 genes into said primarily cultured cell to produce a gene-transfected cell; and selecting a cell by using STRO-1 expression amount at a cell doubling time of 20 and bone regeneration ability as indexes.

Here, the mesenchymal cell is preferably selected from the group consisting of the dental pulp cell, the bone marrow cell, umbilical cell and the adipose cell. The dental pulp cell, the early generated embryo, the bone marrow stem cell, and the umbilical cord cell are as described above. The mammalian animal is also as described above.

Furthermore, the 4 genes are preferably selected from the group consisting of hTERT, bmi-1, E6, E7, Oct3/4, Sox2, Klf4, c-Myc, and p16INK4a. Here, they are preferably hTERT, bmi-1, E6 and E7 for being introduced into the mesenchymal cells. Also, they are 4 genes preferably selected from the group consisting of Oct3/4, Sox2, Klf4, c-Myc, and p16INK4a for being introduced into the somatic cell.

The hTERT is the gene of human telomerase reverse transcriptase, and bmi is also the polycomb group complex which relates to auto-reproduction or control of proliferation of the stem cell. E6 and E7 are the genes existing in the open reading frame encoding the early gene used for the auto-reproduction by human papilloma virus.

The fifth aspect of the present invention is the method for percutaneous absorption for restoring the damaged tissue comprising the steps of: formulating a sheet formed dosage form by resorbing said pharmaceutical preparation for restoring said damaged tissue in a sheet formed moisture-retaining member; covering said damaged site with said sheet formed dosage form; and contacting a positively-charged electrode to a desirable site.

In a specific embodiment, at least 40% of cells obtained after the immortalized stem cells have divided 40 times are STRO-1 positive. Also, since they have the telomere repairing ability, they may divide at least 200 times. Alternatively, they may secrete a variety of the biological factors into the culture sup for long time.

According to the present invention, therefore, the immortalized stem cell which may continuously produce a certain biological factors for long time may be provided.

Also, according to another aspect of the present invention, the pharmaceutical composition and preparation being capable of using for repairing the damaged legion are provided.

Further, the noble percutaneous absorption method for enhancing the absorption rate from the damaged legion is provided.

BRIEF DESCRIPTION OF DRAWINGS

The patent of application file contains at least one drawing executed in color. Copies of this patent or patent application publication with color drawing(s) will be provided by the United States Patent and Trademark Office upon request and payment of the necessary fee.

In FIG. 1, SHED-T shows the immortalized cell, and SHED-C sows non-immortalized cell.

FIGS. 3(A) and (B) are the photographs when the ulcer on the skin is treated. FIG. 3(A) shows the ulcer state before treatment, and FIG. 3(B) shows that of the skin after the treatment.

The mass of newly generated bone area of the newly generated bone/sight area×100.

Figure 4:
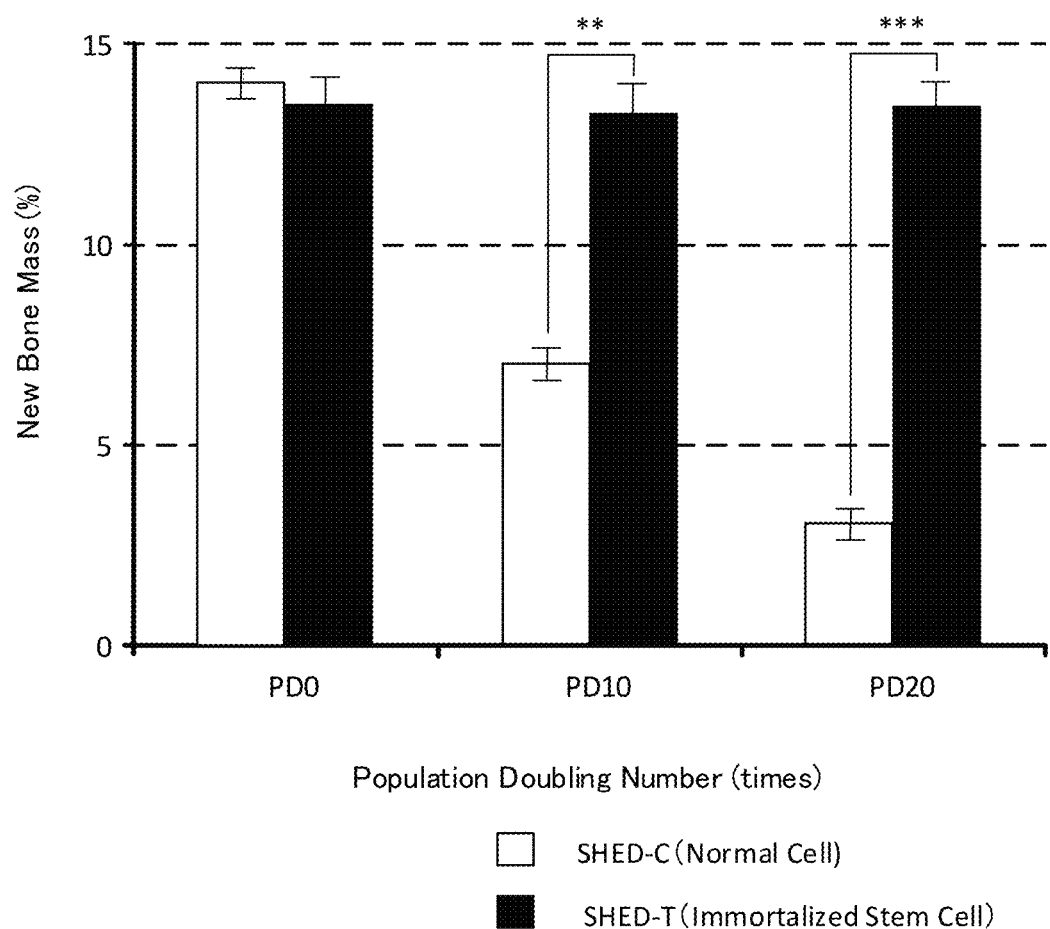
FIG. 4 is the graph showing the relationship between the population doubling time (number of times) and mass of newly generated bone. In the figure,  shows $p<0.05$, * shows $p<0.01$. The mass of newly generated bone are calculated bay using the following equation.

FIGS. 5(A) to (F) show the tissue staining images of SHED-C and SHED-T at each time point of the individual doubling time shown in FIG. 4, when they were transplanted.

FIGS. 6(A) and (B) show photographs showing a recovery of decubitus ulcer. FIG. 6(A) is the skin condition before the treatment, and FIG. 6(B) is that after the treatment.

FIGS. 7(A) to (F) show CT scan images showing the progress of modeling after 1 to 6 months from the implant operation, when the pharmaceutical preparation is used. FIGS. 7(A) to (C) are the images pictured from front view and FIGS. 7(D) to (F) are those from the horizontal direction.

FIGS. 8(A) and (B) show the photographs showing a condition of an alveolar bone of a periodontal disease patient. FIG. 8(A) shows that on the beginning of the treatment (before operation), and FIG. 8(B) shows that after 3 month from the operation.

FIGS. 9(A) and (B) show the photographs showing the result of the osteogenesis in the socket, when β-TCP is used as a scaffold. FIG. 9(A) shows the result of 3 month from teeth extraction, and FIG. 9(B) shows that of implantation performed after 6 months form the teeth extraction.

Figure 10:
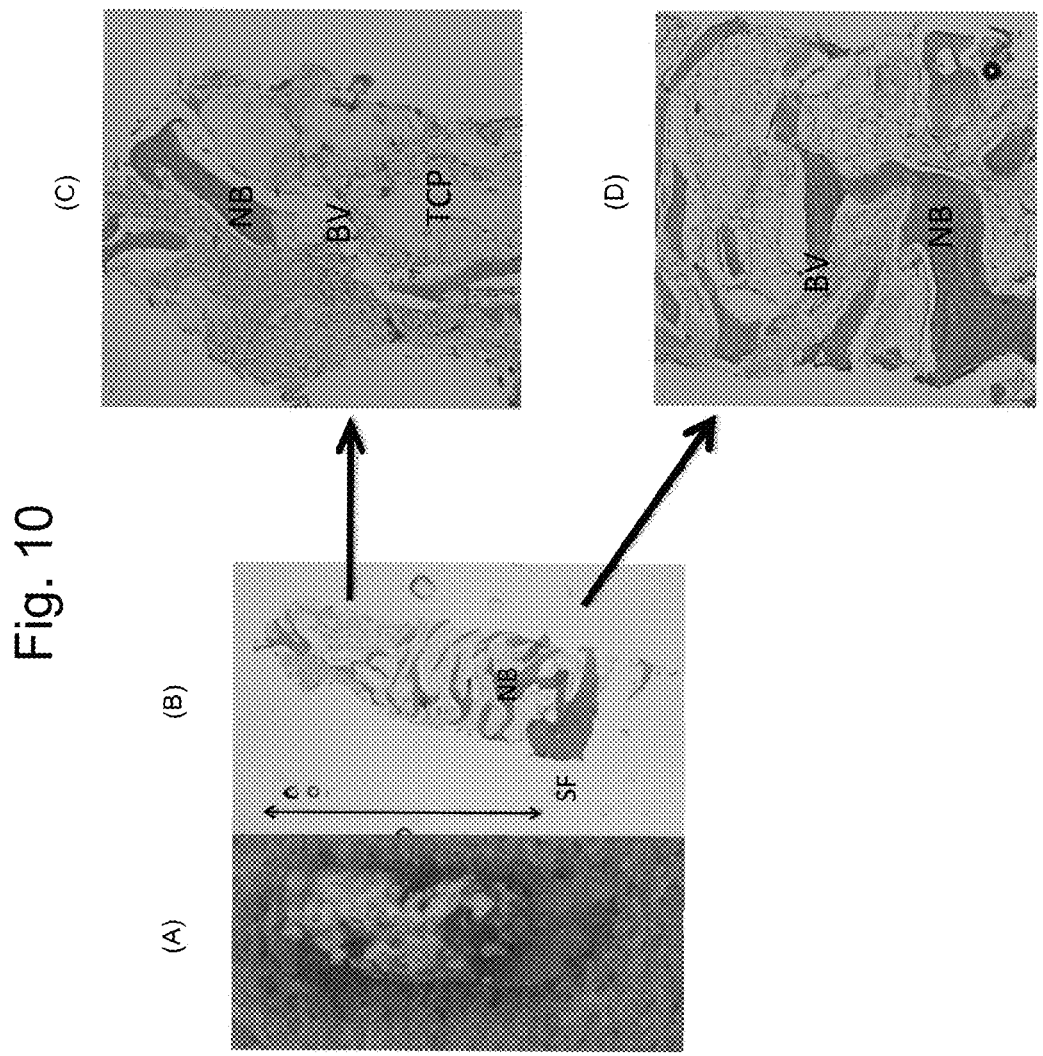

FIGS. 10(A) to (D) shows replacements and others from β-TCP (β-tri-calcium phosphate, $3CaO-P_2O_5$) to the bone, when β-TCP was used as the scaffold. FIG. 10(A) is the photograph showing an excised material, and FIG. 10 (B) is that showing the histochemical result. FIG. 10 (C) and FIG. 10 (D) are partially enlarged images of the pictured images. In the figure, NB shows the new bone, and TCP shows β-TCP. Also, BV shows the blood vessel, and SF shows the bottom of the removed tissue.

Figure 11:
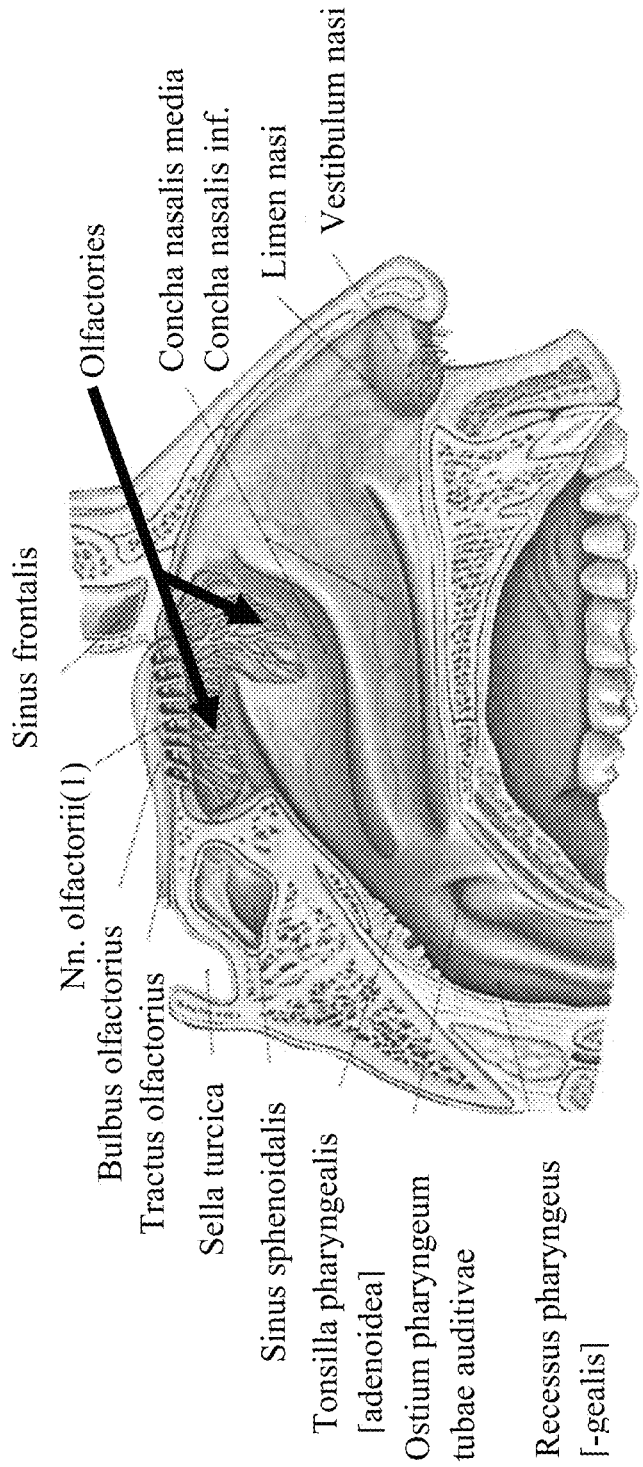

FIG. 11 shows the application site, when the culture sup of the stem cell is administered in i.n. via olfactory bulb.

Figure 12:
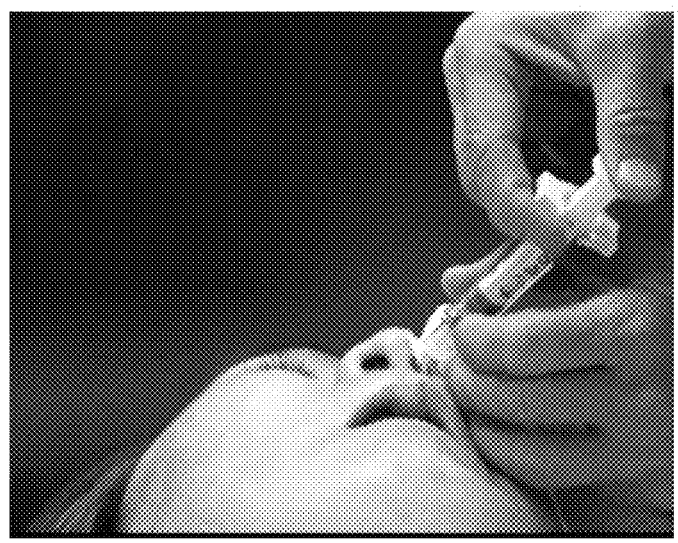

FIG. 12 is the photograph, when the transnasal administration is carried out.

Figure 13:
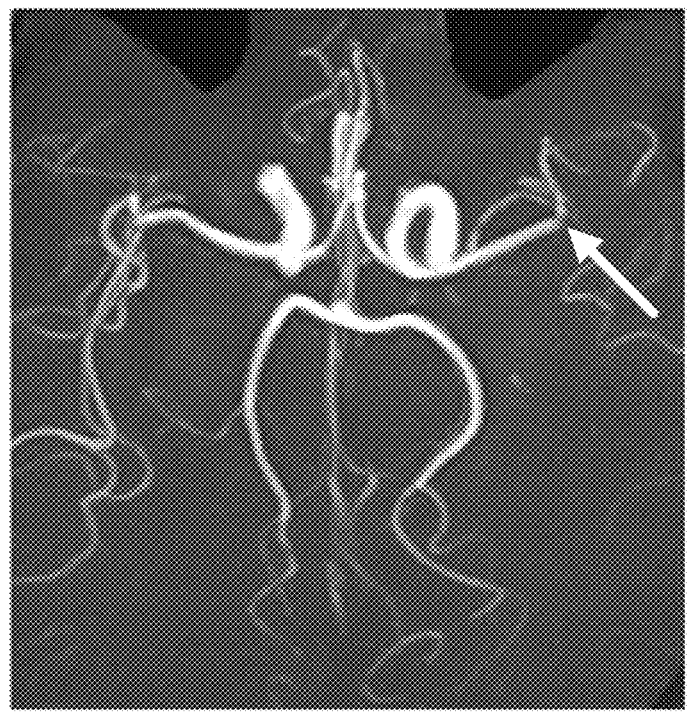

FIG. 13 is MRA image showing the blockage of the blood vessel in the stoke patient.

Figure 14:
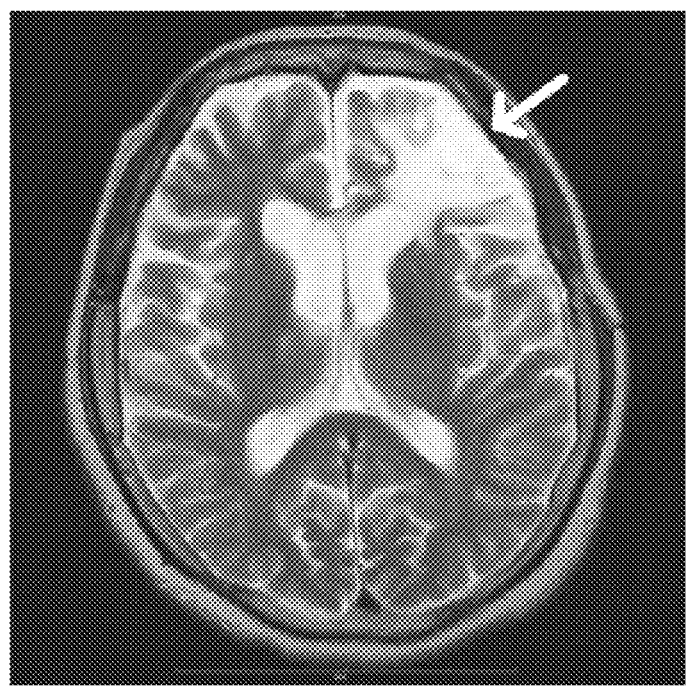

FIG. 14 is CT scan image showing the damaged site of the brain in the stroke patient.

FIGS. 15(A) and (B) are MRI images showing blood stream amount at the damaged site of the brain of stroke patient. FIG. 15(A) is the image immediately after the stroke, and FIG. 15(B) is that after the treatment.

Figure 16:
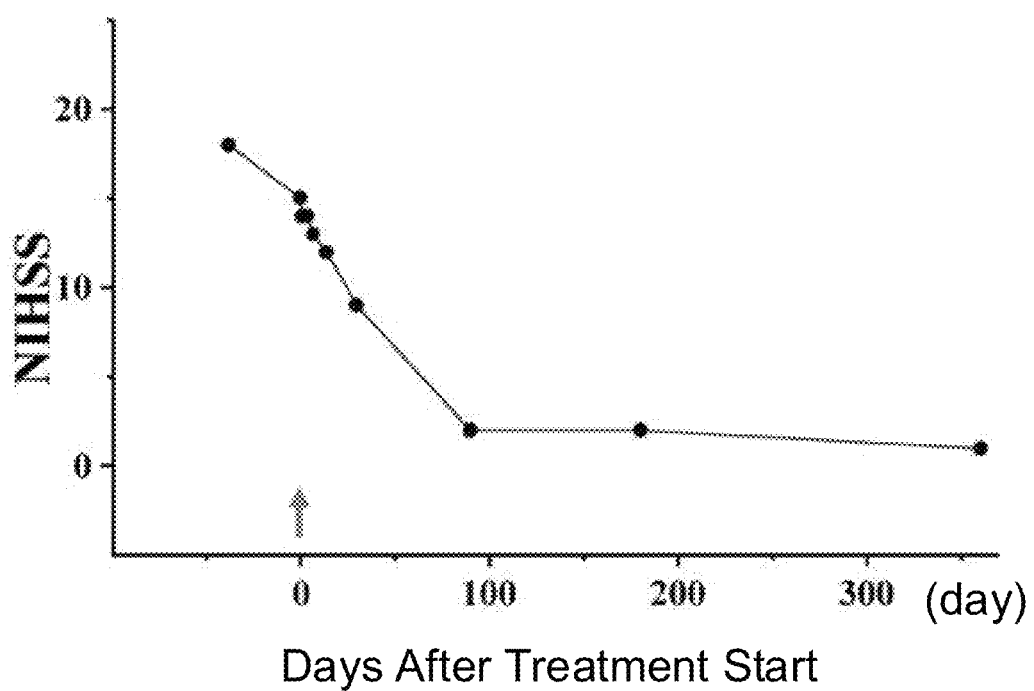

FIG. 16 is the graph showing a score (NIHSS) change, which reflects the conditions of the patient in treatment period.

FIGS. 17(A) and (B) are the photographs showing the function recovery state of the patient. FIG. 17(A) is the photograph showing the recovery status of a hand function, and FIG. 17(B) is that showing the retrieve status of physique.

FIGS. 18(A) and (B) are the result of the time-dependent change after Mini Mental State (Mini Mental State: MMS) or Hasegawa style test were performed for both of an administration group and non-administration group. FIG. 18(A) shows the result of the non-administration group, and FIG. 18(B) shows that of the administration group.

FIGS. 19(A) and (B) are the photographs showing the treatment results against the refractory skin diseases. FIG. 19(A) shows the status before treatment start, and FIG. 19(B) shows that of the treatment finish.

DETAILED DESCRIPTION

The present invention is explained in detail in below.

In order to obtain the immortalized stem cell of the present invention, firstly, the stem cell is isolated from the cell group consisting of a mammalian mesenchymal cell, early generated embryo, and somatic cells except the mesenchymal cell. As the mammal animal, it is preferable to be selected from the group consisting of human, swine, equine, and monkey, because the cells obtained from the mammal are genetically similar to the human cells and are not dangerous for infectious disease.

In the present specification, the terms, "mesenchymal cell", is defined as the cells having differentiation ability into the cells belonging to the mesenchymal such as osteoblast, adipocyte, muscle cell, cartilage cell, and the like. As the specific mesenchymal cell, the dental pulp cell, bone marrow cell, umbilical cell and adipocyte of the above-mentioned animals. Also, the terms, "early-generated embryo", is defined as the embryo in the early stage by the blastocyst, namely, it is in a more progressed stage than the fertilized egg, and necessary for establishing ES cell.

The term, "somatic cell", are defined as the general term of any cell except a germ cell among those being composed of a living body.

Furthermore, the terms, "dental pulp cell", is one of stem cells included in the nerve for the teeth, and has the regeneration ability. Since these cells are protected by hard material, teeth, they do not permeate UV light or radioactive ray and the genes in these cells are not easily damaged. The terms, "bone marrow cell", are defined as the general term for the cells obtained from bone-marrow aspirate, and the bone marrow cell includes a leukocyte series cell such as a myeloblast cell, an erythroblast series cell, a megakaryocyte cell, and plasma cells and the like.

In the present specification, the terms, "umbilical cell", are cells that exists in the umbilical cord, which binds the embryo and a placenta. It is included in the umbilical cord, and also includes umbilical blood. The umbilical cord includes the umbilical blood which enriches hematopoietic stem cells.

As the genes introduced into the stem cells as described above, there are mentioned such as hTERT, bmi-1, E6, E7, Oct3/4, Sox2, Klf4, c-Myc, INK4a, and the like. The gene, hTERT, is a gene for telomere repair enzyme; bmi-1 is the gene of Bmi-1, which is one of proteins being composed of polycomb group complex. Here, Bmi-1 is necessary for maintaining the hematopoietic stem cells with the effect to increase the stem cell by enhancing the activity.

Both E6 and E7 are early genes of either HPV-16 or HPV-18. Also, Oct3/4 is the gene that cooperates with Sox2 to enhance the transcription of the target gene. Klf4 (Kruppel type transcription factor 4) regulates the genes relating to the cell division and the embryogenesis, and it relates to the gastrointestinal system cancer as the tumor suppressor.

Sox2 belongs to the SRY-related HMG box gene family, and is known as the gene that related to the maintenance of undifferentiated functions (totipotency). c-Myc is a cancer promoting gene, and it promotes both of survival and death of the cell in the c-Myc-induced tumor. p16INK4a is the gene which plays important role to control the cell cycle of the tumor cell.

In the following, it is explained as an example for the creation of immortalized cell by using the dental pulp obtained from the human exfoliated deciduous teeth.

Firstly, the exfoliated dens deciduous are disinfected by using a disinfection agent, for example, chlorhexidine, Isodine, and the like. After that, a crown of the tooth is divided in horizontal direction by using, for example, a dental reamer and the like to recover the dental pulp.

Obtained dental pulp tissue is suspended in the basal media, for example, such as Dulbecco's modified eagle's MEM (Dulbecco's Modified Eagle's Medium, herein below, it is referred to as "DMEM") containing 5 to 15% (v/v) of calf serum (calf serum, herein below, it is sometimes referred to as "DMEM"), and 50 to 150 U/mL of antibiotics, and the like. Then, they are treated by using 1 to 5 mg/mL of collagenase at 37° C. for 0.5 to 2 hrs.

As the basal media, DMEM, Iscove's Modified Dulbecco's Medium (IMDM; GIBCO, etc.), Ham's F12 medium, HamF12; SIGMA, GIBCO, etc.), RPMI1640 medium, and the like may be used. Also, a mixed media comprising at least two media may be used. As an example of the mixed medium, there is mentioned that including IMDM and HamF12 in equal amount (for example, it is commercially available under the product name: IMDM/HamF12 (GIBCO)).

As the components to be added to the media, there are mentioned, for example, serum (fetal bovine serum or fetal calf serum, they are referred to as "PBS" or "FCS"), human serum, and sheep serum, serum replacement (Knockout serum replacement (KSR), etc.), bovine serum albumin (BSA), antibiotics such as penicillin, streptomycin and others, vitamins, minerals, and the like.

The basal medium may be also used to culture the selection of cells as mentioned below, and to culture the selected cells.

After enzyme treatment, centrifugation operation is performed for 3 to 10 minutes (3,000 to 7,000 rpm) to recover the dental pulp cell. Depending on the necessity, the cells are selected by using a cell strainer. The selected cells are, for example, resuspended in 3 to 6 mL of the basal medium to plate in a dish having 4 to 8 cm of diameter for adherent cell culture.

Subsequently, the medium, for example, DMEM containing 10% FCS is added, and then the cells are incubated in 5% $CO_2$ incubator at 37° C. for about 2 weeks. After removal of the medium, the cells are washed from 1 to several times with PBS and the like. Instead of the removal of the medium and wash of the cells, the adherent dental stem cells which formed colonies may be collected. The adherent dental stem cells are treated by using a solution including both of 0.025 to 0.1% trypsin and 0.3 to 1 mM EDTA for several minutes at 37° C. to be detached from the dish. Next, detached cells are collected.

After the enzyme treatment, the sample is centrifuged for about 3 to 10 minutes (3,000 to 7,000 rpm) to collect the dental pulp cell. Depending on the necessity, the cells are separated by using a cell strainer. The separated cell is resuspended in 3 to 6 mL of the basal medium for example, to be plated into the dish for adherent cell culture having 4 to 8 cm diameter.

Next, the culture medium, for example, DMEM supplemented with 10% FCS is added; then, they are incubated in a 5% incubator at 37° C. for about 2 weeks. The culture sup is removed, and the cells are washed with PBS in 1 to several times. Instead of removing of the culture medium and washing of the cells, the adherent dental pulp cells forming colonies may be collected. The adherent dental pulp cells are detached from the dish, for example, by using 0.025 to 0.1% of trypsin and 0.3 to 1 mM of EDTA for several minutes at 37° C., and then they are collected.

Subsequently, the selected adherent cells obtained as mentioned above are cultured. For example, the stem cells obtained as mentioned above are plated to the dishes for the adherent cell culture, and then cultured under the conditions of 5% $CO_2$ and at 37° C. in the incubator. By this, primary cultured cells of human exfoliated dens deciduous stem cells (SHED-P) may be obtained.

In passage culture, the cells are collected by using trypsin and EDTA, when the cells become sub-confluent or confluent with macroscopic observation as mentioned above. Then, the cells are plated again in the culture dish including the culture medium.

Here, the term, "sub-confluent", means the situation that the cells adhere about 70% of the bottom area of the culture vessel. For example, the passage is performed 1 to 8 times, and selected cells are propagated up to the necessary cell number, for example, about $1 \times 10^7$ cells/mL. After culturing as described above, the cells are collected to store in liquid nitrogen. The cells collected from a variety of donor may be stored in the form of dental pulp stem cell bank.

Next, the 4 genes are introduced into the primary-cultured cells obtained through the primary culture of the stem cells to create gene-transduced cells. The genes transduced here are preferably 4 types selected from the group consisting of hTERT, bmi-1, E6, E7, Oct3/4, Sox2, Klf4, c-Myc, and p16INK4a. By introducing hTERT, bmi-1, E6, and E7, the immortalized cells having higher population doubling time may be obtained. Here, hTERT is the gene for human telomerase reverse transcriptase; bmi-1 is the polycomb group gene relating to auto-reproduction of the stem cell or differentiation regulation. E6 and E7 are genes existing in an open reading frame coding early gene used to replicate human papilloma virus itself.

Such genes may be introduced as follows.

A plasmid for insertion of the target genes is prepared, and then it is inserted into a shuttle vector, for example, pShuttle2 to clone the genes. *E. coli* is transformed by using the shuttle vector to select kanamycin resistant transformant. Plasmid DNA of the selected kanamycin resistant transformant is purified to identify a recombinant by analyzing restriction sites.

Next, a restriction enzyme, for example, PI-Sce I and I-Cue I are used to cut out an expression cassette from the shuttle vector; then it is ligated into adenovirus vector, for example, Adeno-X viral DNA. Obtained ligation product is cleaved by using Swa I, and it is used to transform the *E. coli*.

Among the obtained transformants, ampicillin resistant transformants were selected. The recombinant adenovirus DNA to which the genes are inserted is purified to identify the transformant by analyzing the restriction sites.

Next, the adenovirus is digested by using Pac I to transfect HEK 293 cells. The recombinant adenovirus is propagated, and then collected to measure their titers. According to a conventional method to purify the virus, it is used to infect the target cell, SHED-P.

Cell population infected with the virus is stained by using FITC according to the conventional method, and then STRO-1 positive cells are detected by using a flow cytometer. Here, STRO-1 is considered as one of markers for the mesenchymal stem cell having pluripotency in the bone marrow, and it becomes an index for cell immortalization.

According to the above-mentioned procedure, the immortalized stem cell from the dental pulp may be obtained.

Next, the obtained immortalized stem cell is cultured in the basal medium, for example, DMEM supplemented with 10% FBS under the condition of 5% $CO_2$ at 37° C. for 24 to 48 hours to obtain the culture sup. In order to collect the culture sup, for example, a Komagome type pipette and the like may be used. The collected culture sup may be used as an active ingredient for the pharmaceutical preparation of the present invention as is. Also, it may be used as that after treatments such as condensation, replacement of the solvent, dialysis, lyophilization, dilution and the like.

As described below, the culture sup of the immortalized stem cell obtained as mentioned above includes a variety of growth factors, and it shows many functions without highly purification. Namely, the composition of the present invention to be used in many diseases may be produced in a convenient process. Therefore, one may avoid to decreasing bioactivities of the growth factors caused by such high purification.

Note that the "culture sup of the immortalized cell" used in the present invention is defined as the culture sup including a variety of biological factors obtained by culturing the immortalized stem cell, and it is the solution which does not include any cells such as the immortalized stem cells and other cells. When the culture sup without sera is prepared, it is preferable to use serum-free medium is used in entire process from initial culture to the passage, or used for several passage prior to collect the cells.

The dental pulp stem cells selected and cultured by using the above-mentioned method are those obtained from the tissue of the living body and has the same properties as the primary cultured cell. In general, the primary cultured cell has similar properties to those of the organ as the source, and it is important that their properties are close to the normal cell. However, it grows slower compared to the lined cell, and sometimes it dedifferentiate during continued culture. Therefore, it is difficult to maintain the cell possessing the properties.

However, the immortalized stem cell of the present invention has significantly higher expression ratio of STRO-1, which becomes the marker of anaplastic degree, compared to that of the dental pulp stem cell which is not the immortalized cell at the time points of population doubling time, 20 or 40. It is preferable that the immortalized stem cell has higher ratio such as about 1.5 to 3, because the high expression ratio of STRO-1 becomes the index that the cell shows the same properties as those of the primary cultured cells.

Also, the immortalized stem cell secretes at least two growth factors selected from the group consisting of insulin-like growth factor (IGF), vascular endothelial growth factor (VEGF), transforming growth factor-$\beta$ (TGF-$\beta$), and hepatocyte growth factor (HGF) into the culture sup. Here, the term "growth factor" is a general term of polypeptides which promote the cell division, bring the morphological change or cell hypertrophy. The growth factors are different depending on the cells that produce them, and they are roughly classified into epidermal growth factor (EGF), fibroblast growth factor (FGF), nerve growth factor (NGF), tumor growth factor (TGF) and the like.

Furthermore, since the receptors on the cell membrane of each cell have tyrosine kinase activity, the binding of the growth factors to them cause the phosphorylation of the tyrosine residues of the proteins and to cause the cell growth or proliferation. It is known that there are several examples that the growth factor becomes a mesoderm inducer in the ontogenesis. Also, it is known that there are several examples that the lymphokine, which modulates the immune system, becomes the mesoderm inducer in the ontogenesis. Such growth factors may be determined by using the known ELISA, microarray assay or the like.

IGF-1 is the polypeptide having a highly similar sequence to insulin, and it causes reactions such as mitogenesis and the like in the culture cells similar to insulin as well. It is also known that IGF-1 affects the nerve cell growth. VEGF is a glycoprotein family involved in vasculogenesis, which newly forms blood vessels in the area wherein the blood vessels are not yet formed in embryonic stage period of embryogenesis, and angiogenesis, which newly forms the blood vessels by branching and extending from already existed the blood vessels. TGF-β also becomes a potent growth inhibitor against the variety of the cells, and tightly involves to the cell differentiation, migration and adhesion, and it plays an important role in a broad region such as ontogenesis, tissue reconstruction, wound healing, inflammation and immunity, cancer invasion and metastasis, and the like. Furthermore, HGF has a variety of physiological activity being involved in the regeneration and protection of the tissue and the organ such as the promotion of the cell proliferation and cell motion, anti-apoptosis (cell death), morphogenetic induction, angiogenesis and others for the various cells including hepatocyte.

Each stem cell mentioned above is cultured, for example, in DMEM supplemented with 15% FCS at 37° C. in the predetermined term, thereby the culture sup including the growth factors as mentioned above may be obtained. Note that the culture sup of the stem cell includes about 70 types of proteins except IGF-1, VEGF, TGF-β, and HGF.

15 mL of the culture sup from the obtained culture sup is poured into Amicon Ultra Centrifugal Filter Units-10K (Millipore Limited). Then, it is centrifuged with ×4,000 g for about 60 minutes to condense about 200 µL Next, the same volume of PBS as the culture sup poured into the tube, and centrifuged again ×4,000 g for about 60 minutes to replace the solvent to PBS. The obtained 200 µL of the solution is collected into the micro test tube to obtain the condensed stem cell culture sup.

Instead of the method by using Amicon as described above, the concentration may be performed by using the following ethanol precipitation method. For example, 45 mL of 100% ethanol is added to 5 mL of the culture sup to mix them and then stood at −20° C. for 60 minutes. After that, it is centrifuged with ×15,000 g for 15 minutes at 4° C. to remove supernatant.

Next, for example, 10 mL of 90% ethanol is added to mix well, and then again centrifuged with ×15,000 g for 5 minutes at 4° C. obtained palette may be dissolved in, for example, 500 µL of the sterilized water. After the dissolution, the entire of the volume is collected in the micro test tube, and the condensed stem cell culture sup is obtained.

The culture sup obtained as mentioned above may be also lyophilized according to the conventional method to have the pharmaceutical preparation to be prepared at time of use.

The content of the growth factor in the culture sup included in the pharmaceutical preparation is preferably about 50 to 500 weight % against the total dry weight thereof. Because, when the content is not more than 50 weight %, it does not exert any effects; and when it is over 500 weight %, the improvement of the effect is not expected.

The dosage form of the pharmaceutical preparation or composition may be in the form including but not limited to powder, liquid, gel, spray, percutaneous system, and the like. For example, the pharmaceutical preparation or composition may be prepared by adding filler, an excipient, an acidity regulator and the like to pour into a small sized container such as a sterile glass ample, serum tube and the like. When using, it is dissolved by using saline or sterile distilled water for injection, and then may be administered via transnasal administration. Alternatively, it is administered by using a sheet of gauze perfused with the solution to adhere the affected area. When it is used for osteogenesis of the alveolar bone and other bones, collagen, β-TCP and others are used as a scaffolding member, which are immersed in the dissolved solution to be embedded.

As the damaged tissues for applying the pharmaceutical preparation of the present invention, there are mentioned such as tissues on which ulcer or decubitus is formed, cerebral tissue damaged by blockage of a blood vessel, and tissues damaged by bone disease, periodontal disease and central nerves system disease, and the like.

Here, the "ulcer" is defined as the tissue deficit site formed on the surface of the organ after being lysed or flaked tissue with necrosis, and it is formed on the epidermis, corium, mucosa and the like. If the tissue deficit toes not reach corium, it is called as erosion. Concretely, ulcer is formed in the area contact with a body surface such as skin, nasal and oral cavity mucosa, cornea and others, or a luminal face of hollow viscus organs such as digestive tract, air passage, urinary tract, blood vessel and others.

The term, "decubitus" is clinically defined as the surrounding tissue of the body surface area which contacts with a supporting surface (mostly, it is bed) has local defective circulation to have necrosis, when the patient put into himself into a state in which he can hold the same position and cannot roll over.

The terms, "deficit caused by a surgical operation", is defined as the deficit which is caused by the surgical operation such as removal of brain tumor and other tumors.

The terms, "blockage of blood vessel" is defined as the state that the blood vessel is blocked by any one of the following reasons. For example, the situation that the blood vessel is narrowed by arteriosclerosis and the blood stream is stopped there; an embolus (clot of blood or fatty acids) is shed from a lining of the blood vessel to block, and the blood stream does not reach the arteriosclerosis site of the blood vessel close to a heart; and blood supply is stopped by the inflammation, cramp, or the change of blood constituent or the blood stream.

The term, "brain" has the functions to memorize, show emotion, make decision and the like. The brain is covered by the fluid called as cerebrospinal fluid. The cerebrospinal fluid (cerebrospinal fluid, CSF) has the role to protect the brain, and transport nutrition and metabolites. The cerebrospinal fluid may be obtained by spinal puncture to the patient, but the properties are depending on the disease of the patient and the like.

Here, the term, "spinal cord", is a nerve trunk of vertebrate. Also, the term, "central nervous system" means the tissue including the spinal cord and the brain. The central nervous system has the functions to work as the reflex center for stimulations from periphery or integrate the stimulations.

The damage of the central nervous system is caused by cord injury and the like. Here, the term, "cord injury" is where the spinal cord is damaged with shock from the outside or internal factors such as a spinal cord tumor, hernia and others. Depending on the severity of the damage, it is classified into a perfect type in which the spinal cord is completely cleaved, and an incomplete type in which the spinal cord is damaged or pressed, but the function of the spinal cord is partially maintained.

The "myelopathy" results from the development of the cervical spondylosis caused by aging (swelling up of an intervertebral disk or forming of spinous process).

The preparation or composition may be applied onto the wound site as a liquid form, or gel form, and it is applied as a sheet formed preparation. Firstly, it is absorbed by a moisture retaining member, for example, gauze, a moisture retaining sheet for medical use and the like to prepare the sheet form preparation. Next, the sheet form preparation put on the wound area so as to cover. A negatively charged rod-shaped electrode is moved on the sheet that covers the wound area, gently rotating the rod. The positively charged electrode is contacted with the desirable area apart from the wound area.

As described above, the active ingredient in the pharmaceutical preparation was effectively administered by utilizing flow of an electric current between the electrode attached onto the wound area, and the electrode contacted to different area from the wound area.

By applying the pharmaceutical preparation of the present invention is applied onto the damaged tissue, it may be possible to recover the tissue quickly.

Example 1

(Creation of the Immortalized SHED and Culturing Method)
(1) Agents for Extraction, Plasmid and the Like
(1-1) Reagent and Others Kanamycin (Kan), ampicillin (Amp), LB liquid medium and LB agar medium, glycogen, agarose, sterilized water, ammonium acetate, sodium acetate, sodium dodecyl sulfate and RNase A were used. Both 50 mg/mL kanamycin (Kan) and ampicillin (Amp) were prepared to store them as stock solutions at −20° C. Glycogen was prepared at the concentration of 20 mg/ml. 10 mg/ml RNase A was prepared to store at −20° C. 10 M (saturated) ammonium acetate ($NH_4OAc$) and 3M sodium acetate (NaOAc; pH 5.2) were prepared.

(1-2) Restriction Enzyme and the Like

E. coli competent cells (Supercharge EZ10 Electro competent Cells, product code 636756), Swa I (the product code 1111A, Smi I is a comparable one), Xho I (the product code 1094A), T4 DNA Ligase (the product code 2011A), Nucleo-Bond Xtra Midi (the product code 740410.10/.50/.100), NucleoSpin Plasmid (the product code 740588 10/50/250) were purchased from Takara Bio Inc. Pac I was purchased from New England Biolabs.

(1-3) Buffer and the Like

1×TE Buffer (10 mM Tris-HCl (pH 8.0) including 1 mM EDTA), which is a mixture of phenol:chloroform:isoamyl alcohol (25:24:1) saturated with 100 mM Tris-HCl (pH 8.0), was prepared. Herein below, it is referred to as "PCI solution". 100% or 70% of ethanol was used. In order to purify pAdeno-X plasmid DNA used in a mini scale recombination, the following buffers 1 to 4 were prepared.

Buffer 1: 25 mM Tris-HCl including 10 mM EDTA and 50 mM glucose (pH 8.0) (after autoclave, stored at 4° C.)

Buffer 2: 0.2M NaOH containing 1% SDS (prepared immediately before the time of use, tightly sealed and stored at room temperature)

Buffer 3: 5 M KOAc (after autoclave, stored at 4° C.)

Buffer 4: 10 mM Tris-HCl (pH 8.0) including 1 mM EDTA and 20 µg/ml of RNase (immediately before use, RNase is added, stored at −20° C.)

(2) Purification of Adenovirus and Reagents for β Gal Assay

HEK293 cells (ATCC #CRL1573) transformed by human type V adenovirus were used. HEK293 cells were cultured in a complete medium. The composition of the complete medium was DMEM (Dulbecco's Modified Eagle's Medium, the basal medium) supplemented with 100 unit/ml sodium penicillin G, 100 µg/ml streptomycin, 4 mM glutamine, and 10% FBS. Sodium penicillin G solution was prepared at the concentration of 10,000 units/ml, and streptomycin sulfate solution was prepared at that of 10,000 µg/ml. They were stored as the stock solutions.

In the culture, 60 mm plates, 100 mm plates, 6-well plate, T75 and T175 flasks were used.

Trypsin-EDTA (the product code CC-5012) was purchased from Takara Bio Inc. Phosphate buffered saline (PBS, without $Ca^{2+}$ and $Mg^{2+}$) and Dulbecco's phosphate buffered saline (DPBS, with $Ca^{2+}$ and $Mg^{2+}$) were prepared. Also, 0.33% neutral red stain solution, and 0.4% trypan blue stain solution were used.

In β-gal assay, X-Gal (5-bromo-4-chloro-3-indolyl-β-D-galactopyranoside (25 mg/ml)) in dimethylformamide (DMF) solution was stored at −20° C. in a light resistant container. Luminescent β-gal Detection Kit II (the product code 631712, Takara Bio Inc.) was used.

(3) Preliminary Test
(3-1) Construction of Recombinant Adenovirus Including lacZ (pAdeno-X-lacZ)

After thawing HEK293 cells and removing DMSO from the solution, HEK293 cells were resuspended in 10 mL of the complete medium. Then, the whole amount was transferred onto the culture plate having a diameter of 100 mm After HEK293 cells adhered to the plate, the culture medium was removed.

Then, the cells were washed once with sterile PBS. After that, 1 ml trypsin-EDTA was added to treat them for about 2 minutes.

Next, 10 ml of the complete medium was added to stop the reaction of trypsin, and then the cells were mildly suspended. By using viable count, 10.sup.5 cells were transferred into the plate having 100 mm diameter including 10 mL medium to spread our evenly.

pShuttle2-lacZ (a positive control vector included in Adeno-X Expression System 1) and Adeno-X Viral DNA (PI-Sce I and I-Ceu I digested) included in the kit was used. According to a protocol attached in the kit, the recombinant adenovirus including lacZ was structured. It was infected to the target cell, SHED, and the expression of β-galactosidase was assayed to confirm that the vector was constructed.

(3-2) Construction of the Recombinant pShuttle2 Plasmid

Prior to the construction of the recombinant pShuttle2 Vector (herein below, it is referred to as "rpShuttle2 Vector".); E. coli DH5a was transformed with pShuttle2 Vector and pShuttle2-lacZ Vector, included in the kit. Transformants were selected on LB agar plate including 50 µg/ml kanamycin (herein below, it is referred to as "LB/Kan".). Bacterial cells obtained from a single colony were streaked on new LB/Kan to be incubated at 37° C. for overnight.

Next, hTERT, bmi-1, E6, and E7 were cloned into pShuttle2. A pShuttle2 vector was cleaved by using a restriction enzyme suitable for these genes.

Next, the multi cloning site matching DNA to be inserted was decided by referring pShuttle2 Vector Information Packet (PT3416-5) attached to the kit. The plasmid treated with the restriction enzyme was treated by using alkaline phosphatase to be purified.

According to the conventional method, target DNA fragments were prepared to be purified. The vector digested with the restriction enzyme and the gene fragments were ligated. By using the ligation product, DH5a cells (competent cell) were transformed. A portion of the competent cell was taken to be transformed by using a control vector, pShuttle2-lacZ Vector included in the kit to use as a positive control.

The mixture including transformed E. coli was plated on the LB/Kan agar plate to select kanamycin resistant (Kanr) transformant (a colony). Five to 10 Kan resistant clones were selected, and they were plated in a small amount of the liquid medium to be amplified. After confirmation that these clones have rpShuttle2 Vector, they were incubated overnight. Then, by using a commercially available silica gel adsorption column, the constructed plasmid DNA was purified according to the conventional method.

The plasmid DNA was treated with the restriction enzyme to be subjected to 1% agarose gel electrophoresis; thereby the target recombinant plasmid was identified. By sequencing, the direction of the inserted fragment and inserted site were confirmed to identify the positive clone.

The recombinant pShuttle2 plasmid DNA (herein below, it is referred to as "rpShuttle2 plasmid DNA") was directly transfected into the target cell, and then it was subjected to Western Blot as a preliminary check the target protein expression.

(3-3) Double Digestion of rpShuttle2 Plasmid DNA with PI-Sce I/I-Ceu I

From the rpShuttle2 plasmid DNA produced as mentioned above, an expression cassette of the inserted gene was taken out by using PI-Sce I and I-Ceu I. According to the in vitro ligation method written in the protocol attached to the kit, the expression cassette which was taken out was integrated into Adeno-X Viral DNA. PI-Sce I/I-Ceu I double-digestion solution for the rpShuttle2 plasmid DNA was prepared 30 It was mixed with the reagents shown in the following Table 1 entered into 1.5 ml of the sterilized micro centrifuge tube.

TABLE 1

| Reagent and others | Liquid measure (µL) | |
|---|---|---|
| | Tube 1 | Tube 2 (lacZ control) |
| sterilized water | 19.5 | 19.5 |
| 10 × double-digention solution | 3.0 | 3.0 |
| rpShuttle2 plasmid DNA (500 ng/µl) | 2.0 | — |
| pShuttle2-lac Z plasmid (500 ng/µl) | — | 2.0 |
| PI-Sce I (1 unit/µl) | 2.0 | 2.0 |
| I-Ceu I (5 unit/µl) | 0.5 | 0.5 |
| 10 × BSA | 3.0 | 3.0 |
| Total | 30.0 | 30.0 |

Next, after fully mixing, the micro centrifuge tube was lightly centrifuged, and then incubated for 3 hours at 37° C.

The double digested reaction mixture (5 µl) was subjected to 1% agarose/EtBr gel electrophoresis together with 1 kb ladder (DNA size marker).

(3-4) Extraction by Phenol:Chloroform:Isoamyl Alcohol

The remains of the double-digestion solution (25 µl), 70 µL 1×TE Buffer (pH 8.0) and 100 µL PCI mixture were added into the centrifuge tube, the tube was mixed by using a vortex. Then, the tube was centrifuged by using a micro centrifuge at 4° C. with 14,000 rpm for 5 minutes. Then, the aqueous layer was transferred to 1.5 ml of clean centrifuge tube. Here, 400 µL of 95% ethanol, 25 µL of 10 M ammonium acetate, and 1 µL glycogen (20 mg/ml) were added, and then mixed by using the vortex.

Next, it was centrifuged at 4° C. with 14,000 rpm for 5 minutes. Then, the supernatant was removed by aspiration to obtain a pellet. 300 µL of 70% ethanol was added on the pellet, it was centrifuged for 2 minutes with 14,000 rpm. The supernatant was carefully aspirated to remove, the pellet was air dried about for 15 minutes.

After the pellet was dried, it was dissolved in 10 µL sterilized 1×TE Buffer (pH 8.0), and the solution was stored at −20° C.

(4) Construction of the Recombinant Adeno-X Plasmid DNA (4-1) Subcloning of the Expression Cassette into Adeno-X Virus Genome The reagents shown in the following Table 2 were sequentially added into the 1.5 ml of the sterilized micro centrifuge tube. Then, it was mildly mixed and lightly centrifuged. After that, it was incubated at 16° C. for overnight.

TABLE 2

| Reagent and others | Liquid measure (µL) |
|---|---|
| PI-Sce I/I-Ceu I digested pShuttle2 plasmid DNA | 2.0 |
| PI-Sce I/I-Ceu I digested pShuttle2-lac Z plasmid DNA | — |
| sterilized water | 3.0 |
| 10 × DNA Ligation Buffer | 1.0 |
| Adeno-X Viral DNA(250 ng/µl) | 3.0 |
| DNA Ligase(1 unit/µL) | 1.0 |
| Total | 10.0 |

90 µL of 1×TE Buffer (pH 8.0) and 100 µL of PCI mixture were added to each sample, and then it was mildly mixed by using vortex. It was centrifuged at 4° C. with 14,000 rpm for 5 minutes, and the aqueous layer was transferred to 1.5 mL of the clean microcentrifuge tube. Then, 400 µL of 95% ethanol, 25 µL of 10 M ammonium acetate solution, and 1 µL of glycogen (20 mg/ml) were added to the tube, and then it was mildly mixed by using the vortex.

It was subjected to the centrifugation at 4° C. for 5 minutes with 14,000 rpm, and the supernatant was removed by the aspiration to obtain the pellet. The following ethanol precipitation operations were the same as those of (3-4).

After drying, the pellet was dissolved in 15 µL of the sterile deionized water.

(4-2) Swa I Digestion of the Recombinant Adeno-X Plasmid DNA

The digestion solution as shown in the following Table 3 was prepared, and added into each sample in the centrifuge tube. Then, they were incubated for 2 hours at 25° C.

TABLE 3

| Reagent and others | liquid measure (µL) |
|---|---|
| ligation product | 15 |
| 10 × Swa I Digestion Buffer | 2.0 |
| 10 × BSA | 2.0 |
| Swa I (10 units/µL) | 1.0 |
| Total | 20.0 |

80 µL of 1×TE Buffer (pH 8.0) and 100 µL of PCI mixture were added to each sample, and then it was mildly mixed by using the vortex. The following ethanol precipitation operations were the same as those of (3-4), and the dissolved solution of the pellet was stored at −20° C. until use.

(4-3) Confirmation of the E. coli Transformant by the Recombinant Adeno-X Plasmid DNA The electroporation competent cells (E. coli) were transformed with the Swa I digested products obtained in (4-2) by using Supercharge EZ10 Electrocompetent Cell (the product code 636756).

The transformant mixture was plated on the agar plate, which is the mixture of LB medium and ampicillin (final conc. 100 µg/mL) (herein below, it is referred to as "LB/Amp agar plate".), and then they are incubated at 37° C. for overnight. About $10^6$ of colonies were obtained as ampicillin resistant (Ampr) transformant.

The obtained colonies were checked by using Adeno-X System PCR Screening Primer Set attached to the product.

The bacterial cells from the single colony were plated in 5 mL of fresh LB/Amp liquid medium, and incubated overnight. The next day, according to the mini-scale method as mentioned below, Adeno-X plasmid DNA was purified.

(4-4) Mini-Scale Preparation of the Recombinant Adeno-X Plasmid DNA 5 mL of log-phase culture medium was centrifuged with 14,000 rpm for 30 seconds to remove the supernatant. The pellet was centrifuged at 10,000 rpm for 1 minute again, and then the supernatant was removed by using the micropipette.

150 µL of the buffer 1 was added and mildly pipetted to resuspend. 150 µL of the buffer 2 was added into the cell suspension. Then the cell suspension was mildly inverted to mix and stood for 5 minutes on ice 150 µL of the buffer 3 was added to the cooled cell suspension, and then it was inverted to mix again and stood for 5 minutes on ice.

The cell suspension was centrifuged at 4° C. with 14,000 rpm for 5 minutes, and the clear supernatant was transferred into 1.5 ml of the clean centrifuge tube. 450 µL of PCI mixture was added to the supernatant, and then inverted to mix. Then, it was centrifuged at 4° C. with 14,000 rpm for 5 minutes, and the aqueous layer was transferred to the clean 1.5 ml of the micro centrifuge tube.

The following ethanol precipitation operations were the same as those of (4-1), and the dissolved solution of the pellet was stored at −20° C. until use. The rDNA of the interest was identified by using the analysis with the restriction enzymes and PCR as described below.

(5) Restriction Site Analysis of the Obtained rAdeno-X Plasmid DNA

Analysis was performed by using PI-Sce I and I-Ceu I. The reagents shown in the following Table 4 was added to a 1.5 ml micro centrifuge tube. Then, 30 µL of PI-Sce I/I-Ceu I double digestion solution was added to it, and then fully mixed and then it was lightly rotated to collect the contents.

TABLE 4

| Reagent and others | liquid measure (µL) |
| --- | --- |
| sterilized water | 19.5 |
| 10 × double-digestion solution | 3.0 |
| rpAdeno-X DNA (500 ng/µl)(500 ng/µl) | 2.0 |
| pShuttle2-lac Z plasmid (500 ng/µl) | — |
| PI-Sce I (1 unit/µl) | 2.0 |
| I-Ceu I (5 unit/µl) | 0.5 |
| 10 × BSA | 3.0 |
| Total | 30.0 |

It was incubated at 37° C. for 3 hours to perform restriction treatment. The reaction mixture after the treatment was subjected to 1% agarose/EtBr gel electrophoresis.

(6) Production of the Recombinant Adenovirus (6-1) Preparation of the rAdeno-X Plasmid DNA for HEK293 Cell Transfection The reagents shown in the following Table 5 were transferred into the 1.5 ml of the sterilized centrifuge tube to be mixed, and then it was lightly centrifuged by using the micro centrifuge. Then, it was incubated at 37° C. for 2 hours to treat the rAdeno-X plasmid DNA with Pac I restriction enzyme.

TABLE 5

| Reagent and others | liquid measure (µL) |
| --- | --- |
| sterilized water | 20 |
| pAdeno-X plasmid DNA (500 g/µl) | 10 |
| 10 × Pac I Digestion Buffer | 4 |

TABLE 5-continued

| Reagent and others | liquid measure (µL) |
| --- | --- |
| 10 × BSA | 4 |
| Pac I (10 units/µL) | 2 |
| Total | 40 |

60 µL of 1×TE Buffer (pH 8.0) and 100 µL of PCI mixture were added to it, and then they were mildly mixed by using the vortex. Then, it was centrifuged by using the micro centrifuge at 4° C. for 5 minutes with 14,000 rpm. The aqueous layer was carefully transferred into 1.5 ml of the clean sterilized centrifuge tube.

The following ethanol precipitation operations were the same as those of (3-4), and the dissolved solution of the pellet was stored at −20° C. until use.

(6-2) Transfection of Pac I Digested Adeno-X Plasmid DNA into HEK293 Cell

Before 24 hours of the plasmid DNA transfection, HEK 293 cells were plated on the 60 mm culture plate so as that the cell number was about 1 to $2 \times 10^6$ (about 100 cells/mm²). Then, they were incubated at 37° C. under the presence of 5% $CO_2$.

10 µL of Pac I-digested Adeno-X plasmid DNA was transfected to each culture plate to introduce Adeno-X DNA into the HEK293 cell, according to a standard transfection method (CalPhos Mammalian Transfection Kit, the product code 631312, Takara Bio Inc.). Occurrence of CPE (cytopathic effect) was confirmed from the next day of the transfection.

One week later, the cells adhered on the bottom or side wall of the culture plate was released by mild mixing. The obtained cell suspension was transferred into a 15 mL sterilized centrifuge tube having a conical bottom, and it was centrifuged at room temperature for 5 minutes with 1,500×g.

Obtained precipitate was suspended in 500 µL of the sterilized PBS. The solution was subjected to the free-thaw operation for 3 times, which is frozen in dry ice/ethanol and thawed in the incubator with 37° C., to obtain the lysate in which the cells were fully thawed. Next, it was lightly centrifuged to remove suspended matter, and then the supernatant was transferred into the sterilized another tube to use immediately. The lysate not immediately used was stored at −20° C.

250 µL of the lysate was added onto the cultured cells in a 60 mm plate culturing was continued. Note that by using anti-Hexon antibody included in Adeno-X Rapid Titer Kit (the product code 631028, Takara Bio Inc.), the adenovirus was titrated according to the instruction manual (PT3651-1) of the kit.

(6-3) Virus Amplification for Preparing the Virus Having High Titer

Before 24 hours of the titration start, HEK293 cells were plated on a T75 flask, and they were incubated at 37° C. in the presence of 5% $CO_2$ for overnight to be confirmed that they became 50 to 70% of confluent.

In the next day, the medium was exchanged to that including the virus for infection with the virus at MOI=10. After the incubation at 37° C. in the presence of 5% $CO_2$ for 90 minutes, the flask was taken out and 10 mL of the medium was added into the flask.

They were cultured at 37° C. for 3 to 4 hours in the presence of 5% $CO_2$, and CPE was confirmed. After 50% of the cells were released, the released cell suspension was prepared as described above; it was transferred to a 15 mL sterilized centrifuged tube with the conical bottom. The freeze and thaw operation as described above was performed, and the cells were thawed. By using Adeno-X Rapid Titer Kit (the product code 631028), the titer, $10^7$ PFU/mL was obtained.

Western blotting was performed, and it was confirmed whether the packaged adenovirus genome has copies of the specific transcription unit against the target gene as the functional form.

(7) Adenovirus Infection to the Target Cells
(7-1) Infection to the Target Cells Before 24 hours of the infection, $1 \times 10^6$ cells of SHED were plated on a 6-well plate. In the next day of the plating, the medium was removed, and 1.0 mL of the medium including virus was added to the center of each well in the plate. The solution was spread on a monolayer formed by the SHED.

It was incubated at 37° C. for 4 hours under the presence of 5% $CO_2$, and the virus was infected to SHED. Next, the fresh medium was added, and then incubated at 37° C. in the presence of 5% $CO_2$ From 24 to 48 hours after the infection, the expression of the introduced gene was analyzed time dependently.

(7-2) Analysis of the β-Galactosidase Expression of the Infected Cells

The β-galactosidase expression in the adherent cell infected with the Adeno-X-lacZ was assayed by using Luminescent β-gal Detection Kit II (the product code 631712, Clontec Laboratories Inc.).

Example 2

(1) Manufacturing of SHED

An exfoliated dens deciduous from a 10 year old healthy boy was used. After the exfoliated dens deciduous was disinfected with Isodine solution, a crown of the teeth was horizontally cut by using the dental diamond point, and then the dental pulp tissue was collected by using the dental reamer. The obtained dental pulp tissue was digested in the solution including 3 mg/mL of type I collagenase and 4 mg/mL of disperse at 37° C. for 1 hour. Next, the solution was filtrated by using 70 mm of cell strainer (Falcon).

The filtered cells were resuspended in 4 mL of the medium to be plated into the culture dish having the 6 cm of diameter. DMEM (Dulbecco's Modified Eagle's Medium) including 10% FCS was added into the dish and cultured for about 2 weeks in the incubator prepared as 5% $CO_2$, at 37° C. The adherent cells formed colonies (the dental pulp stem cells) were treated by using 0.05% trypsin-0.2 mM EDTA for 5 minutes at 37° C., and then the cells released from the dish were collected.

Next, the adherent cells selected as mentioned above were plated on the culture dish for the adherent cells (a collagen coat dish), and they were incubated in the incubator prepared under 5% $CO_2$ at 37° C. as the primary culture to obtain the primary cultured cell. When the cells became macroscopically sub-confluent (about 70% of the surface of the culture container was covered by the cells), or confluent, the cells were treated by using 0.05% trypsin-0.2 mM EDTA at 37° C. for 5 minutes to be released from the container, and then collected.

Thus obtained cells were again plated on the dish including the medium, and perform passage in several times to be grown to achieve the cell number, about $1 \times 10^7$ cells/mL. The obtained cells were stored in the liquid nitrogen.

After that, by using the primary cultured cells, the passage was performed at the cell concentration at $1 \times 10^4$ cells/cm$^2$.

In the experiment, the cells passed from 1 to 3 were used. The human BMMSC (the bone marrow mesenchymal stem cell, Bone Marrow Mesenchymal stem cells) was purchased from Lonza Group Ltd. and cultured according to the instruction manual provided from the manufacturer.

As described above, the human exfoliated dens deciduous dental pulp stem cells (SHED) were obtained. Among the obtained SHED, about $1 \times 10^6$ cells of STRO-1 expression cells were sorted from each sample by using FACSTAR-PLUS (Becton, Dickinson and Company).

According to the manufacturer's instruction manual of the bromodeoxyuridine BrdU staining kit (Invitrogen), BrdU was incorporated into the cells during 12 hours to evaluate the growth rate of SHED (n=3 in each group). The experiments were repeated for 5 times. After one-way analysis of variance, Tukey-Kramer test was performed to evaluate statistical significant difference.

In order to detect STRO-1 with immunofluorescence, SHED was fixed by using 3% paraformaldehyde, and rinsed twice with PBS and then treated by using 100 mM of glycine for 20 minutes. Next, these cells were permeabilized with 0.2% of Triton-X (Sigma-Aldrich) for 30 minutes. Then, they were incubated in the mixture of 5% donkey serum and 5% of bovine serum albumin for 20 minutes.

Next, the cells were incubated with the primary antibody, mouse anti-human STRO-1 antibody (1:100, R&D Inc.) for 1 hour, then incubated with the secondary antibody, goat anti-mouse immunoglobulin M-FITC antibody (1:500, Southern Biotech Corp.) for 30 minutes, and then mounted by using Vector Shield DAPI (Vector Laboratories Inc.).

After that, .alpha.-MEM supplemented with 15% of FBS was added to the 6 well plate, and then the sorted cells were plated in each well for preparing clones. About 300 colonies among the proliferated cells were pooled for the test.

(2) Transgenesis

As described above, 4 genes, bmi-1, E6, E7 and hTERT were integrated into the adenovirus vector to manufacture a virus vector to express the gene products. As a reference, the control vector to which these genes were not integrated was manufactured.

SHED was plated on the collagen coat dish having 100 mm of the diameter at the concentration of $1 \times 10^6$ cells, and then DMEM supplemented with 10% FBS was added. They were cultured until sub-confluent. The medium was removed by aspiration, and 500 μL of the virus solution diluted with the medium was added (MOI=10), and then incubated at 37° C. for 1 hour in the 5% $CO_2$ incubator for the virus vector infection. After 48 hours from the infection, the medium was exchanged to the above-mentioned one. The infected cells were incubated for 10 days in the medium supplemented with puromycin (1 pg/mL) to select the resistant clone, and the 500 to 600 of resistant clones were pooled. In every 3 to 4 days, about $0.5 \times 10^5$ SHED cells were plated to the culture dish having 100 mm φ of the diameter to perform passage. SHED cells to which the genes were transferred were named SHED-T, and SHED cells to which the genes were not transferred were named SHED-C.

Example 3

(1) Measurement of the Growth Rates of SHED-C and SHED-T

Figure 1:
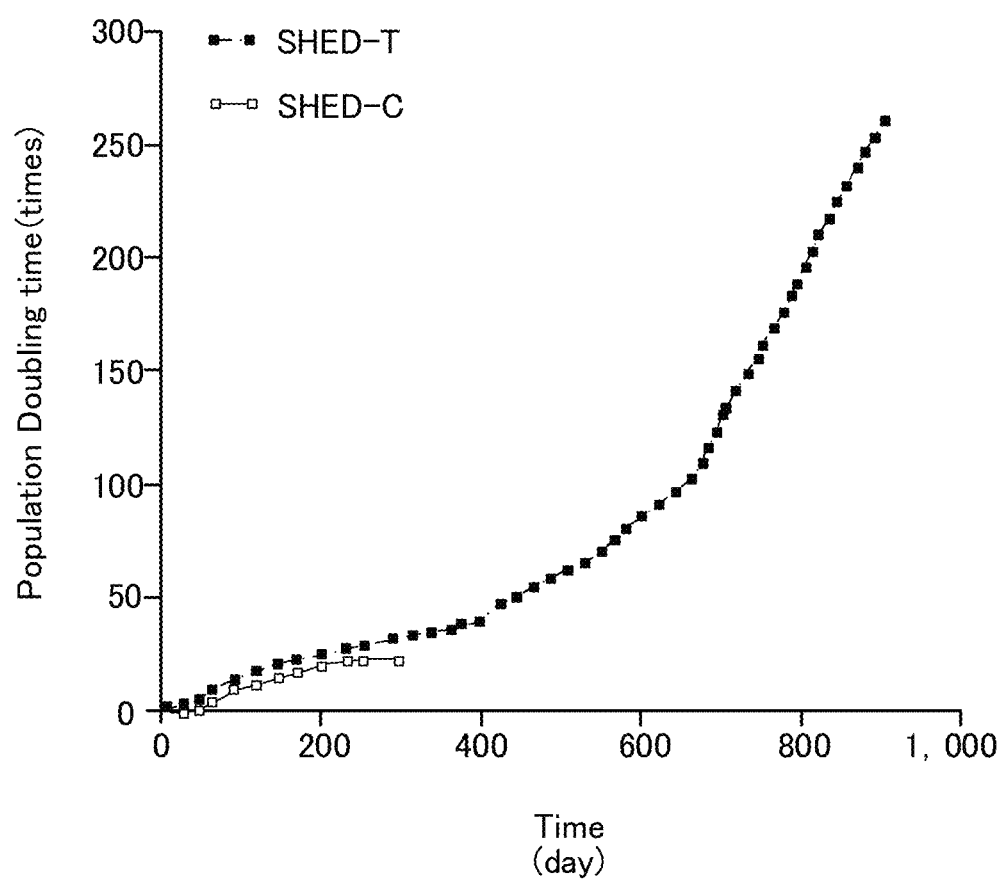
FIG. 1 is a graph showing a relationship culturing times of population doubling times (population doubling time, herein below, it is referred to as "PD") between the immortalized stem cell and non-immortalized stem cell.

Status of the population doubling time of SHED-T (the gene transferred SHED) was shown in FIG. 1. In the figure, a vertical axis shows the population doubling time number (cell division number, times), and an abscissa axis shows the time period (date of culture). Evaluation standard for the aging was the status wherein SHED in culture does not divide for 1 month.

The growth of SHED-C has stopped about 30 times to enter aging or proliferation termination phase. In contrast, SHED-T passed over and proliferated after 800 days has passed.

(2) Flow Cytometry Analysis

Figure 2:
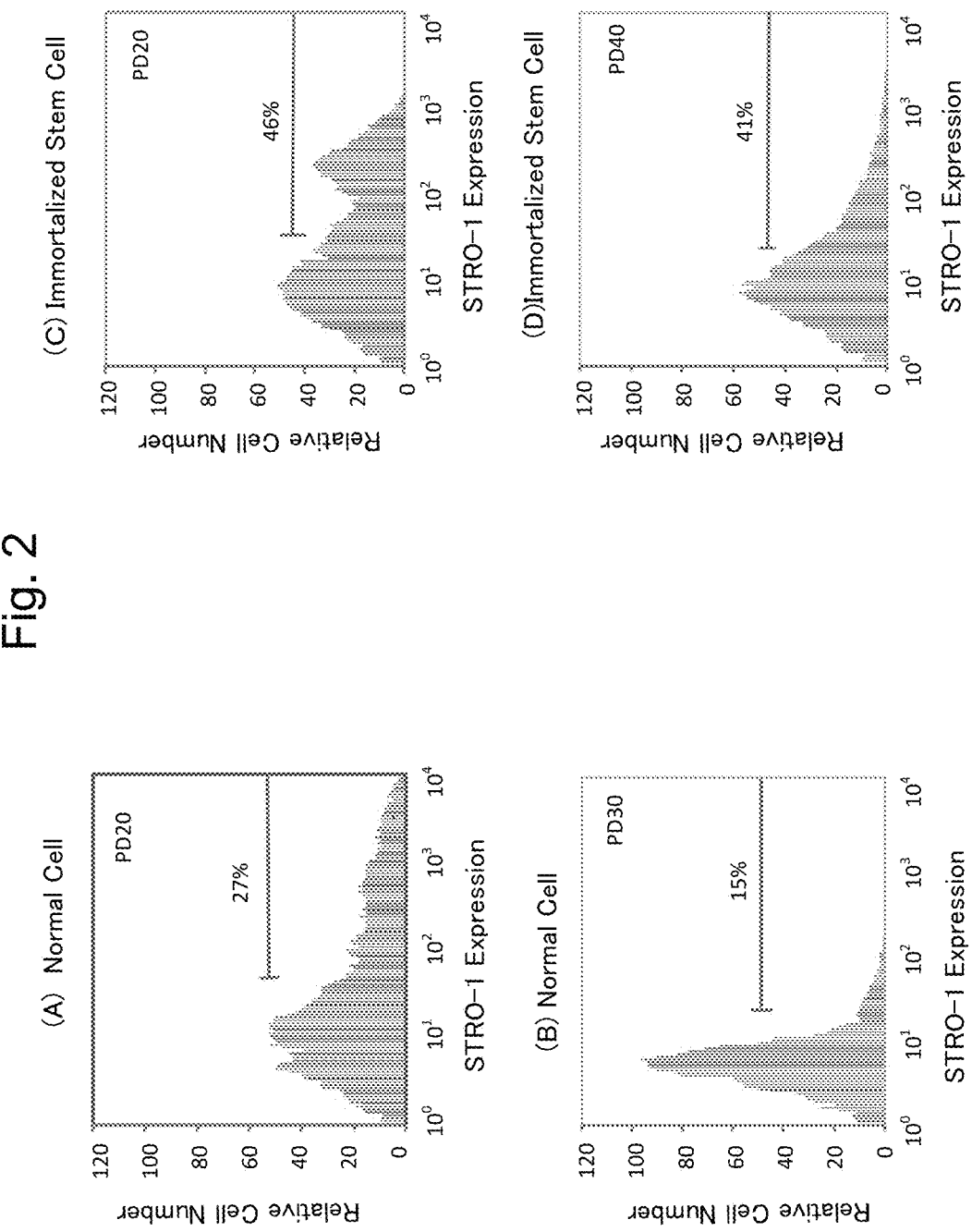
FIGS. 2(A) to (D) are the graphs showing results of STRO-1 expression in both SHED-C and SHWD-T (see, FIGS. 2(A) to (D)). Wherein, PD20 means that the doubling time is 20, PD30 means that it is 30, and PD40 means that it is 40.

In order to obtain a single cell suspension, the adherent monolayer cells were digested with trypsin/EDTA. The anti-STRO-1 monoclonal antibody (1:100) was added to $2\times10^5$ cells and stood to analyze by using FACS Calibur flow cytometer (Becton, Dickinson and company). When the fluorescence level of them was higher more than 99% in the ratio compared to the control antibody with corresponding to the same isotype, the expression was positive. In both of SHED-T and SHED-C, the primary and later passage cells were fixed, and stained with FITC binding STRO-1 antibody. Then, it was analyzed by using the flow cytometry. The test was repeated twice. In SHED-C, the ratio of the STRO-1 positive cells was 27% at PD20, and decreased 15% at PD30 (FIGS. 2(A) and (B)). The ratio of the STRO-1 positive cells in SHED-T was 46% at PD20 and 41% at PD40, respectively (FIGS. 2(C) and (D)).

(3) Study for the Differentiation Ability

The differentiation abilities of SHED-C or SHED-T at PD0, PD10 and PD20 were studied by using the forming ability of the new bone mass and histological stain of the tissue.

Firstly, $2.0\times10^6$ SHED-C or SHED-T cells were mixed with 40 mg of ceramic powder of hydroxyapatite/tricalcium phosphate (HA/TCP) (Olympus Corporation), and then the mixture was inoculated subcutaneously under a dorsal surface of immunocompromised mouse at 10 weeks age (NIH-bgnu-xid, female, Harlan Sprague Dawley Inc.).

Eight weeks after the inoculation, the inoculant was recovered, and fixed by using 4% formalin to decalcify. Then, it was buffered by using PBS solution including 10% EDTA for paraffin embedding. A part of it was stored in 70% ethanol for embedding in resin.

Figure 5:
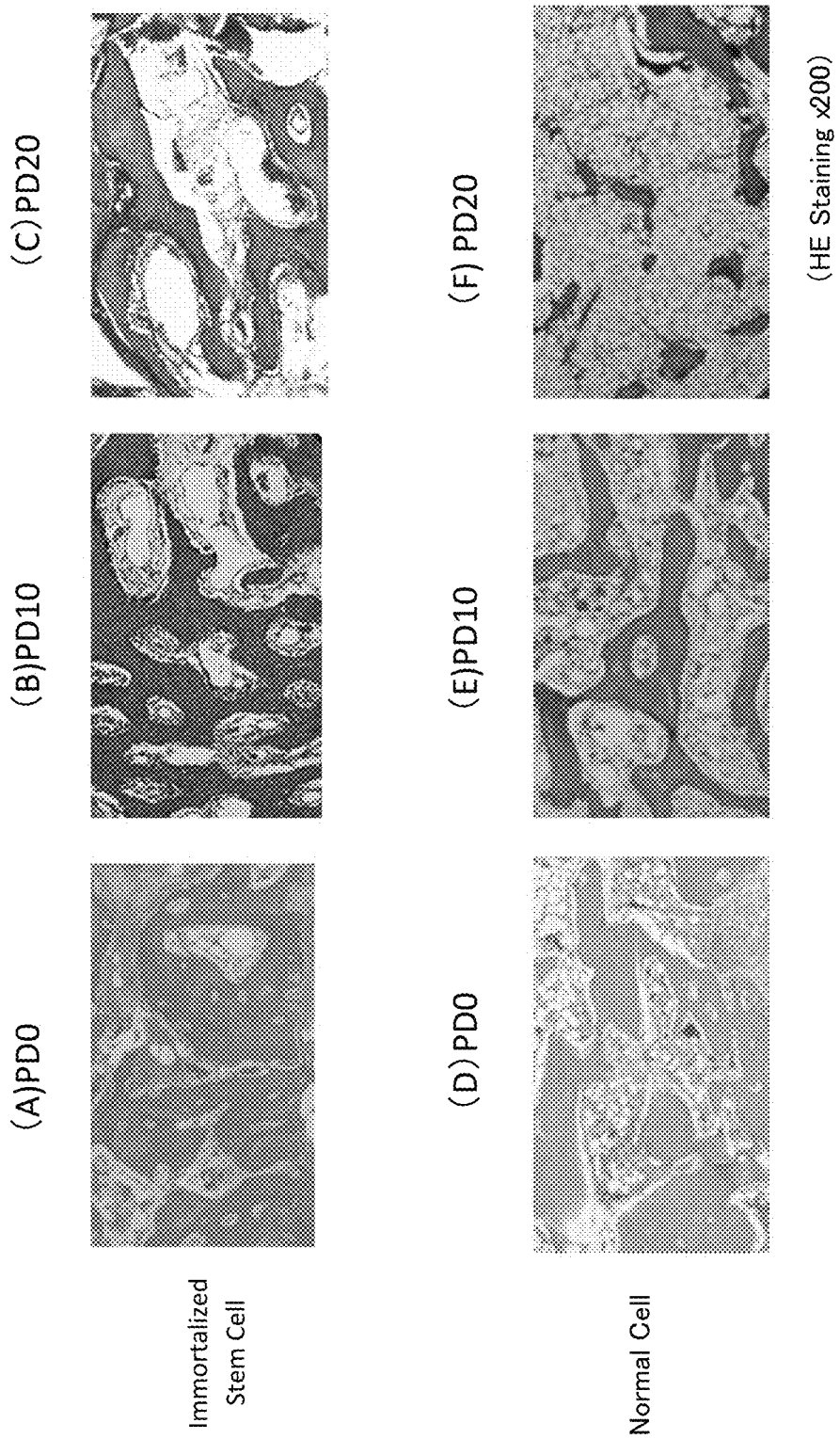

A paraffin section was deparaffinized, and hydrated. After that, the section was stained with hematoxylin and eosin (herein below, it is referred to as "H&E".). FIGS. 5(A) to (C) show the stained images of SHED-T (the immortalized stem cell) at PD0 to PD20, and FIGS. (D) to (F) show the stained images of SHED-C (the normal cell) at PD0 to PD20. In order to determine the new bone formation in vivo, the specified positions were chosen, and the area of the new bone and the sight area were calculated to obtain the new bone mass from these values for the inoculant formed after SHED-T inoculation or SHED-C inoculation.

New bone mass=New bone area/sight area×100

FIG. 4 shows the change of the new bone mass of SHED-T and SHED-C at each population doubling number (doubling time). In the figure,  shows p<0.05, * shows p<0.01. Note that the new bone mass was obtained by using the following equation.

As shown in FIG. 4, the new bone mass was decreased depending on the increase of the population doubling time in SHED-C, and it was decreased to about ⅕ at PD20 compared to that of PD0. In contrast, the bone mass was not changed by PD20 in SHED-T, and the bone mass in SHED-T showed 5 times higher than that of SHED-C at PD20.

(4) Evaluation of Tumor Formation Activity $1\times10^6$ cells of SHED-C cells or SHED-T cells were inoculated to the subcutaneous tissue of the immune compromised mice. After inoculation, cells were observed for more than 30 days. However, the tumor was not formed during the observation term in any mice to which the cells were transplanted. Also, all of the clones from the cultured cells did not show any morphological change between the ranges from 40 to 200PD in SHED-T cells.

By this, it was demonstrated that SHED-T had no tumor forming activity.

(5) Evaluation

It was demonstrated that SHED-T had proliferation ability, holding differentiation ability even after 260PD. However, SHED-C had the differentiation ability, but had aged not over than 30PD.

As described above, it was demonstrated that SHED-T became the immortalized stem cell, and is suitable for large scale production of SHED supernatant having higher activity.

Example 4

(1) Curative Effect for Radiation Ulcer in Cervical Region

A 64 years old (male) tongue cancer patient (right side tongue (T3N0M0)) had a surgical operation of hemiglossectomy. After 6 months, since metastasis was found in the lymph node of the right side neck, the patient received radiation of 60 GY and performed total neck dissection. After 3 weeks of the dissection, the incomplete wound healing was occurred from a submandibular to the neck, and the ulcer was formed (FIG. 3(A)). Therefore, it was diagnosed as a radiation neck ulcer.

In order to promote the wound healing, 10 mL of the culture sup of SHED-T obtained as mentioned above was immersed into a sheet of gauze with the size to cover the affected area. Then, it was attached on the affected area. Once every two days, the gauze with the culture sup was exchanged 14 times. After 1 month, the ulcer was closed (FIG. 3(B)). From the above, it was demonstrated that the culture sup had a curative effect on the ulcer.

(2) Curative Effect Against the Decubitus

The decubitus formed on the hip of the 60 year old man was treated with the culture sup of SHED-T. The man had the stroke 2 years ago, and became hemiplegia. In order to treat the decubitus, he came to the hospital.

A granulation tissue with the infection (FIG. 6(A)) was completely removed; 10 mL of SHED-T culture sup was impregnated without dilution to cover the affected area. The gauze was exchanged every day. After 2 weeks, new epidermis was formed from the edge of the skin so as to cover the affected area (FIG. 6(B)).

From the above, it was demonstrated that the culture sup had a curative effect to the ulcer and the decubitus.

Example 5

(1) Curative Effect of SHED-T Culture Sup in the Dental Field

The curative effects of the culture sup of SHED-T in the dental field was studied at 28 sites of total 16 patients (35 to 70 years old) composed of 11 men and 5 women.

Detail of the cases was that 14 patients (18 sites) relate to the implant, and 7 patients (10 sites) relate to periodontal disease. The detail of implant related patients was that 11 patients relate the guided bone regeneration (GBR)-socket preservation (15 sites), and 3 patient s relate to Sinus-lift (3 sites).

Here, GBR (guided bone regeneration) procedure is the treatment method for promoting the regeneration of the bone tissue such as the defected alveolar bone, jawbone and the like. It is utilized when there is insufficient amount of bone for embedding the implant. Also, the socket preservation is the method for regenerating the bone by inserting the artificial bone and the like into the "hole" at the time of teeth extraction for preventing the bone resorption.

Sinus-lift (the sinus floor augmentation) is performed when maxillary sinus existing inside of upper jawbone enlarged, and the thickness of the certain part of the alveolar bone became insufficient for the implant operation. It is the technique to push the bottom part of the maxillary sinus by inserting the osseous graft or bone prosthetic material, recently a part of the implant body is used, into the site of the maxillary sinus having insufficient thickness.

Evaluations of the tested cases were performed 26 sites until the September 2011 by using X-ray (including CT) at 3 month or 6 month from the operation. They were evaluated in the following 5 classes. Results were shown in Table 6, FIGS. 7(A) to 7(F), FIGS. 8(A) to 8(B), and FIGS. 9(A) to 9(B).

In FIG. 7(A), it was observed that the powdery β-TCP was packed in the part shown in a white arrow. In contrast, in FIG. 7(C), the structure of the same part shown in the arrow was changed to become structureless as the same as the bones located in the lower side. It was demonstrated to promote the bone formation.

Also, it was observed that the granulation tissue was formed on the part shown in the white arrow, not but the bone and immature bone was formed in the part shown in the black arrow in FIG. 7(D). In contrast, it was confirmed that the part shown in the black arrow became mature bone, and promoted the osteogenesis in FIG. 7(F).

From the above, the osteogenesis promotion in the dental field was confirmed.

5 (remarkable): the osteogenesis was found more than 30% of the defected part 4 (effective): the osteoanagenesis was found in the defected part (less than about 30%)

3 (no change): the osteoanagenesis was not clear but any bone resorption 2 (resorption): the bone resorption was found 1 (poor): the heavy bone resorption was occurred or adverse event

| No. | patient | age | sex | site | Operation | date of operation | duration (month) | scaffold | evaluation | adverse event |
|---|---|---|---|---|---|---|---|---|---|---|
| 1 | HS | 46 | F | L56 | osteoanagenesis | 2011 Feb. 11 | 11 M | artificial bone | 5 | No |
| 2 | KT | 60 | M | ⌐6 | osteoanagenesis | 2011 May 16 | 8 M | collagen | 3 | No |
| 3 | KT | 60 | M | 2⌐ | osteoanagenesis | 2011 May 16 | 8 M | collagen | 4 | No |
| 4 | YF | 40 | M | ⌐7 | osteoanagenesis | 2011 May 23 | 8 M | collagen | 3 | No |
| 5 | YF | 40 | M | ⌐6 | regeneration* | 2011 May 23 | 8 M | collagen | 3 | No |
| 6 | HN | 35 | M | 7⌐ | osteoanagenesis | 2011 May 30 | 8 M | artificial bone | 4 | No |
| 7 | TO | 45 | F | ⌐56 | osteoanagenesis | 2011 May 30 | 8 M | artificial bone | 4 | No |
| 8 | TY | 70 | M | 1⌐ | osteoanagenesis | 2011 Jun. 13 | 7 M | collagen | 4 | No |
| 9 | AM | 66 | M | 43⌐ | regeneration* | 2011 Jun. 13 | 7 M | collagen | 3 | No |
| 10 | TT | 51 | F | 7⌐ | osteoanagenesis | 2011 Jun. 25 | 7 M | collagen | 5 | No |
| 11 | TS | 59 | M | L7 | osteoanagenesis | 2011 Jul. 4 | 6 M | artificial bone | 5 | No |
| 12 | TS | 59 | M | L6 | regeneration* | 2011 Jul. 4 | 6 M | artificial bone | 4 | No |
| 13 | EO | 59 | F | ⌐45 | regeneration* | 2011 Jul. 25 | 6 M | collagen | 3 | No |
| 14 | EO | 59 | F | L67 | regeneration* | 2011 Jul. 25 | 6 M | collagen | 4 | No |
| 15 | NK | 58 | M | ⌐567 | osteoanagenesis | 2011 Aug. 1 | 5 M | collagen | 5 | No |
| 16 | HS | 67 | F | ⌐5 | osteoanagenesis | 2011 Aug. 8 | 5 M | collagen | 5 | No |
| 17 | HS | 67 | F | 5⌐ | osteoanagenesis | 2011 Aug. 8 | 5 M | collagen | 5 | No |
| 18 | HS | 67 | F | 7⌐ | osteoanagenesis | 2011 Aug. 8 | 5 M | artificial bone | 5 | No |
| 19 | KM | 51 | M | 7⌐ | osteoanagenesis | 2011 Aug. 8 | 5 M | collagen | 5 | No |
| 20 | MK | 63 | M | 1⌐1 | osteoanagenesis | 2011 Aug. 29 | 5 M | artificial bone | 2 | No |
| 21 | HM | 61 | M | ⌐67 | regeneration* | 2011 Aug. 29 | 5 M | collagen | 4 | No |
| 22 | HM | 61 | M | 76⌐ | regeneration* | 2011 Aug. 29 | 5 M | collagen | 5 | No |
| 23 | TS | 59 | M | 6⌐ | regeneration* | 2011 Aug. 30 | 5 M | collagen | 3 | No |
| 24 | TS | 59 | M | 6⌐ | regeneration* | 2011 Aug. 30 | 5 M | collagen | 3 | No |
| 25 | TS | 59 | M | 7⌐ | osteoanagenesis | 2011 Aug. 30 | 5 M | collagen | 3 | No |
| 26 | TM | 64 | M | L567 | osteoanagenesis | 2011 Sep. 13 | 4 M | artificial bone | 5 | No |
| 27 | NK | 58 | M | 7⌐ | regeneration* | 2012 Jan. 23 | 0 M | collagen | — | No |
| 28 | TY | 70 | M | 1⌐ | osteoanagenesis | 2012 Jan. 24 | 0 M | artificial bone | — | No |

Among 28 cases, the case No. 27 and 28 were not evaluated because there was not the time for evaluation. All cases evaluated (26 cases), remarkable (5) was 10 cases (38.5%), effective (4) was 7 cases (26.9%), no change (3) was 8 cases (30.8%), resorption (2) was 1 case (3.8%), and adverse effect (1) was 0 cases.

The sum of the remarkable and effective cases was 17 (65.4%), and a response rate was high.

In detail of each disease, the remarkable (5) was 9 (52.9%), the effective (4) was 4 (23.5%), no change (3) was 3 (17.7%), the resorption (2) was 1 (5.9%) and the adverse event (1) was 0 in the implant related cases. Therefore, in the implant cases, the sum of the remarkable and effective cases was 13 (79.4%), and the response rate was very high.

In 9 cases related to the periodontal disease, the remarkable was 1 (11.1%), the effective was 3 (33.3%), the no change was 5 (55.6%), and the resorption and adverse event were none. In the periodontal disease related cases, the sum of the remarkable and the effective cases was 4 (44.4%), and the response rate was good.

Furthermore, depending on the scaffold, in 8 cases having the β-TCP scaffold, the remarkable was 4 (50.0%), the effective was 3 (37.5%), the no change and the adverse effect were none, and the resorption was 1 (12.5%). When the β-TCP was used as the scaffold, the sum of the remarkable and effective cases was 7 (87.5%), and the response rate was excellent high.

In 18 cases, Terudermis or Teruplug (Col) was used as the scaffold, and the remarkable were 6 (33.3%), the effective were 4 (22.2%), the no change was 8 (44.5%), the resorption was 1 (0.1%), and the adverse event was none. When Terudermis or Teruplug (Col) was used as the scaffold, the sum of the remarkable and effective cases was 10 (55.5%), and the response rate was high.

Figure 7:
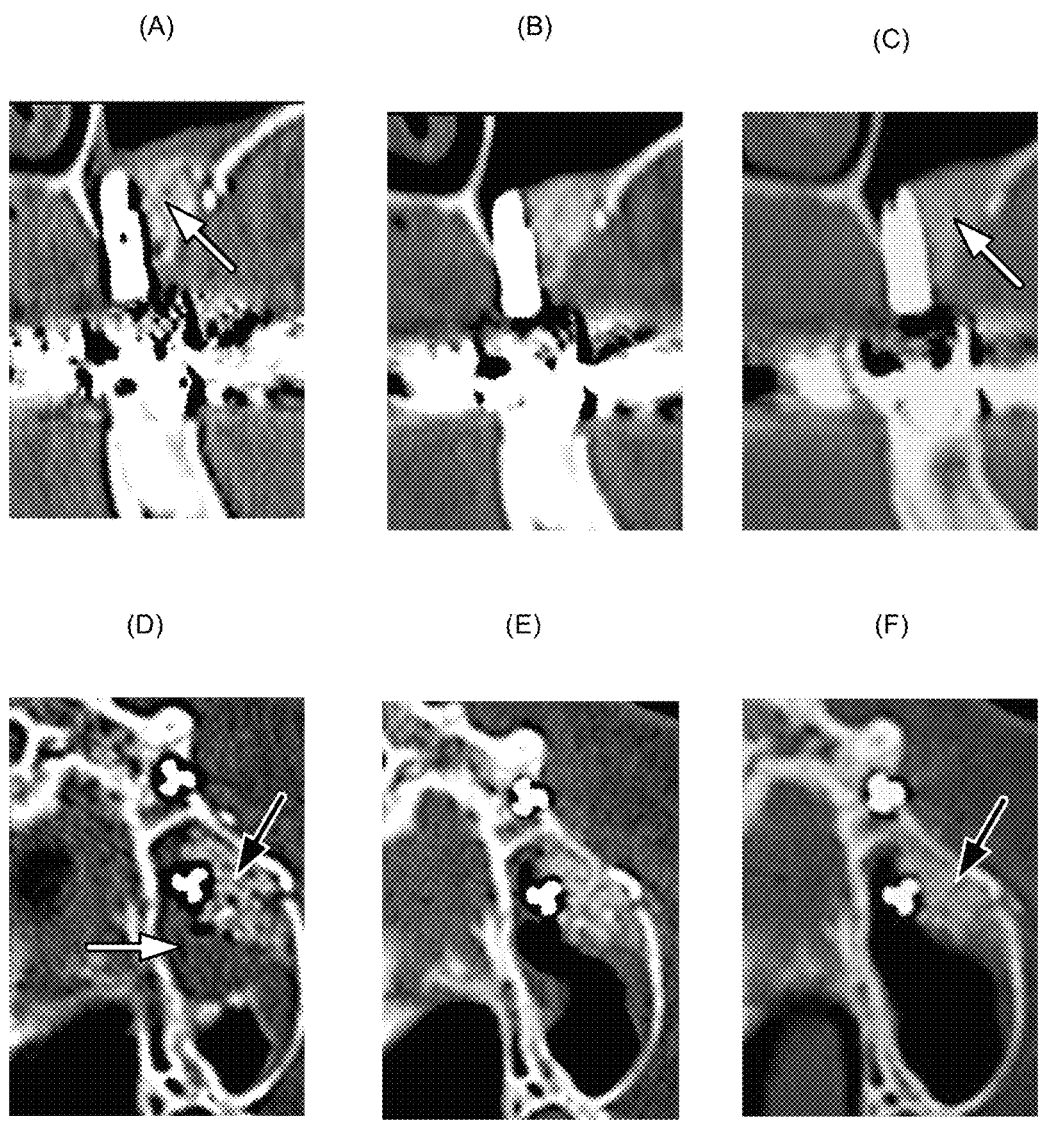

In the implant cases, as shown in FIGS. 7 to 9, all of the cases showed the bone regeneration.

Also, when β-TCP was used as the scaffold, it was confirmed by using hematoxylin and eosin staining of the tissue how the replacement of β-TCP to the bone and the like was happened. The results are shown in FIGS. 10(A) to (D). In the figure, the new bone formation shown as NB was clearly observed, and also the blood vessel shown as BV was found.

From the above, it was confirmed that the culture sup of SHED-T has osteogenesis ability.

Example 6

(1) Intranasal Administration of the Cytokines Derived from the Dental Pulp Stem Cell to the Stroke Patients The culture sup of SHED-T was administered to 8 patients having ischemia in gray matter, ischemia in white matter, or ischemia in mixed region (6 men, 2 women) for studying treatment effects. All eight patients got the standard treatment before joining the clinical trial. They were diagnosed with MRI, and had neurological test and evaluated by using NIHSS score. For the patients shown in the Table 7, it was administered 20 to 1410 days after symptoms developed of the stroke. Profiles of the patients were shown in the following Table 7.

SHED-CM (the culture sup of SHED-T) prepared in the example 1 was given with intranasal administration from the site which it the point that olfactory nerves in nasal cavity collected (FIGS. 11 and 12). The administration period was counted from the administration start.

Recovery statuses were evaluated by a neurosurgeon or neurologist at the time point of 1 day, 2 days, 4 days, 7 days, 14 days, 1 month, 3 month, 6 month and 1 year from the administration start. Blind tests were not performed. For all of the patients, MRI and MRA of the brain were performed. MRA is referred to as magnetic resonance angiography, and it is the test to show the status of the blood vessels as a stereo image. The MRA image and the MRI image of one patient were shown in FIG. 13 or FIG. 14, respectively.

Blood oxygenation level, body temperature, blood pressure, heart rate, breathing rate and the like before and after the administration of the culture sup of SHED-T were carefully monitored by using electro cardiogram. Chest X-ray photography was also performed before and after the administration.

Before the intranasal administration of SHED-CM and 1 year later, the magnetic resonance angiography was performed for all patients for specifying the vascular legion, and observed images pictured by using colored nuclear magnetic resonance imaging (MRI). The neurological status was scored on the basis of National Institute of Health Stroke Scale (NIHSS).

In 2 patients (both were in acute phase) among 8 of them, remarkable recoveries at NIH standard and the MRI images were found (FIGS. 15(A) and 15(B), and FIG. 16). The patient No. 2 recovered so as to transship cups by using paralyzed right hand and arms as shown in FIG. 17(A), and to become ambulatory as shown in FIG. 17(B).

In any patients who received SHED-CM, the tumor, abnormal cell growth in the central nervous system, and neurological deterioration were not observed. Also, in the any patients, there were no trouble in the noses, systemic malignant tumor, and systemic infectious disease.

From the above, it was demonstrated that the culture sup could be infinitely obtained by using the immortalized stem cell. It was also demonstrated that this enabled the production of large amounts of the growth factors, when the pharmaceutical preparation is produced by using the culture sup. By this, there is the merit that this permits the low cost production of the pharmaceutical preparation.

As mentioned above, it is possible to maintain the content amount and the types of the growth factors in the sup of the cells almost constant, because the particular immortalized stem cell is used as the cell source, and the stem cell continues to produce the particular growth factors sustainably. By this, there is the merit that the components contained in the culture sup are easily standardized, when the sup is produced in large scale.

TABLE 7

| No. | Patient | sex | age | symptom | date of occurrence | start date | date before start (day) | stage | result |
|---|---|---|---|---|---|---|---|---|---|
| 1 | DM | M | 31 | hemiplegia | 2010 Mar. 24 | 2011 Apr. 9 | 381 | chronic | unchanged |
| 2 | TK | M | 58 | hemiplegia | 2011 Mar. 22 | 2011 Apr. 9 | 20 | acute | remarkable |
| 3 | NO | M | 72 | hemiplegia | 2007 Jun. 1 | 2011 Apr. 11 | 1410 | chronic | unchanged |
| 4 | YS | F | 70 | hemiplegia | 2010 Sep. 1 | 2011 May 9 | 250 | chronic | unchanged |
| 5 | IM | M | 58 | hemiplegia | 2010 Sep. 27 | 2011 Sep. 6 | 344 | chronic | unchanged |
| 6 | AU | F | 72 | hemiplegia | 2010 Mar. 25 | 2011 Sep. 19 | 543 | chronic | unchanged |
| 7 | MK | M | 55 | hemiplegia | 2010 Nov. 6 | 2011 Oct. 8 | 336 | chronic | unchanged |
| 8 | KT | M | 60 | hemiplegia | 2010 Dec. 10 | 2011 Jan. 10 | 31 | acute | remarkable |

Example 7

(1) Intranasal Administration of the Cytokines Derived from the Dental Pulp Stem Cell to Alzheimer Patients SHED-T was intranasally administered to the Alzheimer patients to study the treatment effect. The average age of the patients, 3 women, were 79.5±3.

The culture sup of SHED-T was administered i.n. once a day in total 28 times. The results of the administration were evaluated by using the mini mental state examination and Hasegawa's dementia scale shown in the following Tables 8 and 9.

As shown in FIG. 18(A), in the non-administration group, there was no large improvement even when either MMS or Hasegawa's was used for the evaluation.

In contrast, in the culture sup of SHED-T administration group, an index value began to increase after 3 month. After 7 month, the increase rate became larger in both MMS and Hasegawa's to achieve symptomatic relief of Alzheimer disease.

Among the patient group, one Alzheimer patient at 78 years old showed remarkable improvement. The patient had cerebral infarction on May 11, Heisei 22, and serious amnesia appeared (Cornell Medical Index: CMI=27). Therefore, she entered the care facility on December 20, Heisei 22.

From February 9, Heisei 23, the culture sup of SHED-T was administered i.n. once a day in total 28 times. Then, the results of the administration were evaluated by using the mini mental state examination and Hasegawa's dementia scale shown in the following Tables 8 and 9. Excellent improvement of higher brain function was found. Since the patient recovered sufficiently to cook for herself and to walk on her own, she discharged from the care facility and back to own home on April 16, Heisei 23.

TABLE 8

| Mini Mental state test questions (Mini Mental State: MMS) |
| --- |
| Questions |
| 1. Date & time (5 points) |
| What year is this? What season is now? What day of the week is today? What is the date today? |
| 2. Present location (5 points) |
| Which prefecture are you? Which city are you? Which hospital are you? Which district are you? |
| 3. Memories |
| Three goods names with no relationship are give to the patient and make he/she repeat as is 1 point is given 1 answer If no right answers, repeat 6 x |
| 4. 7 series |
| Sequentially subtract 7 from 100 5 points given to 5 times completion Stop this when mistake made |
| 5. Remember (3 points) |
| make repeat the names of goods provided in 3 again |
| 6. Names (2 points) |
| A clock and a pencil are sequentially shown to the patient, and make him/her answer |
| 7. Read characters (1 point) |
| Repeat the following sentence "Everyone draw a net ashore together" |
| 8. Understand of instruction (3 points) |
| The following 3 instructions are given tree orally, and execute after finishing to hear "Take a paper on your right hand" "Fold the paper in half" "Put it on a table" |
| 9. Understanding the sentence (3 points) |
| After reading the sentence, act the contents written "Close the clothes" |

TABLE 8-continued

| Mini Mental state test questions (Mini Mental State: MMS) |
| --- |
| Questions |
| 10. Writing sentence (1 point) |
| Please write a sentence. |
| 11. Comprehension of figures |
| Trace the following figures |

From the above, the culture sup of SHED-T has advantageous effect for Alzheimer disease.

Example 8

(1) Treatment Effect of the Culture Sup of SHED-T Against Hepatitis

A radical treatment for serious liver disease such as decompensated cirrhosis and the like is a liver transplant. However, only symptomatic therapy is performed, because of reasons such as donor shortage and the like. In order to cover this, a liver regeneration therapy was performed by administering the growth factors derived from the immortalized deciduous teeth stem cell (SHED-T).

TABLE 9

| No | Questions | Answers |
| --- | --- | --- |
| 1 | How old are you? (Error under 2 years are acceptable) | Right 1 Wrong 0 |
| 2 | What is the date today of what year? What day of the week is today? (If the year, month, day, and day of the week are right, 1 point is given to each right answer) | Year, month, day, and the date of the week, for each right 1 wrong 0 |
| 3 | Where we are? (If voluntarily give answer, give 2 points. If not, wait 5 seconds, provide the branches, "Your home? Hospital? Care facility?". If he/she chooses right one, give 1 point.) | Voluntarily gives an answer 2 Give the answer for the branches 1 Wrong answer 0 |
| 4 | Please say 3 words which I will say. Also, since I will make the same questions, please memorize. Say the following one. 1): a) Chery blossom b) cat c) train 2): a) plum b) dog c) bicycle | For each a), b), and c) Right 1 Wrong 0 |
| 5 | Please subtract 7 from 100 sequentially. Make questions such as 'subtract from 100? Then again subtract 7? If the first answer is wrong, the test will stop. | For either one, Right answer 1 Wrong answer 0 |
| 6 | Please say the number said in reverse. State that "you will say the number 6-8-2, 3-5-2-9" in reverse sequence. If the patient fails to say 3 orders in reverse sequence, you will terminate the test. | For each, Right 1 Wrong 0 |
| 7 | Please say the words you memorize again. Voluntarily answer, give 2 points for each. If no answer, provide the following branches. Give 1 point for the right answer. Hint: a) a plant b) an animal c) a vehicle | For each a), b), and c) Right (voluntarily) 1 point Right answer with a hint 1 point Wrong answer 0 |

TABLE 9-continued

| No | Questions | Answers |
|---|---|---|
| 8 | I will show you 5 goods from now, and hide them. Please say what you saw. Provide unrelated goods such as a clock, a tobacco, a key, a pen, a coin or the like. | 5 Right 5<br>4 Right 4<br>3 Goods are right 3<br>2 Goods are right 2<br>1 Good is right 1<br>No wrong answer 0 |
| 9 | Please say the name of vegetables as many as possible. Write the vegetable names on the sheet. If paused more than 10 seconds, terminate this test. | 10 names raised 5<br>9 names raised 4<br>8 names raised 3<br>7 names raised 2<br>6 names raised 1<br>not more than 5 names 0 |

Subjects were 3 male patients without active period hepatoma (58 to 70 years old), but Child-Pugh not less than 7, total bilirubin not more than 3.0 mg/dL, and platelet number not less than $5.0 \times 10^{10}$ as shown in Table 10. Note that the patients were in chronic phase cerebral infarction, and they had treatment for Parkinson's disease (at least 1 year passed from the symptom appearance.).

In a protocol, the growth factors derived from the immortalized deciduous teeth stem cell (2 μg) was dissolved in 5 mL of saline and administered intranasally every day. 1 protocol has 28 times and 2 protocols were performed.

The details of the disease and results are shown in Table 11.

TABLE 10

|  | 1 point | 2 points | 3 points |
|---|---|---|---|
| liver encephalopathy | No | light | often coma |
| Ascites | No | little | Medium |
| serum bilirubin (g/dl) | not over 2.0 | 2.0 to 3.0 | over 3.0 |
| serum albumin (g/dl) | over 3.5 | 2.8 to 3.5 | not over 2.8 |
| prothrombin time (%) | over 70 | 40 to 70 | not over 40 |
|  |  | Child-Pugh classification | A 5-6 points<br>B 7 9 points<br>C10-15 points |

TABLE 11

| | | | | Before operation (mg/dl) | | | 12 Month later (mg/dl) | | |
|---|---|---|---|---|---|---|---|---|---|
| No. | Patient | Age | Disease Name | CP*1 | TP*2 | Alb*3 | CP*1 | TP*2 | Alb*3 |
| 1 | A | 70 | alcoholic hepatitis | 7 | 7.5 | 2.8 | 5 | 8.5 | 3.4 |
| 2 | B | 58 | hepatitis B | 7 | 6.5 | 2.9 | 5 | 8.0 | 3.5 |
| 3 | C | 65 | unknown | 7 | 5.0 | 2.4 | 5 | 6.5 | 3.8 |

*1 Child-Pugh value
*2 total protein
*3 albumin (2) Result

In any patients, both of total protein content and serum albumin level were increased, and CP changes from B class to A class. Therefore, it was considered that the liver was regenerated.

Example 9

(Treatment Effects by the Culture Sup of SHED-T Against Type II Diabetes)

The treatment effects by the SHED-T for the type II diabetes were studied. In the protocol, the growth factors derived from the immortalized deciduous teeth stem cell (2 μg) was dissolved in 5 mL of saline and administered intranasally every day. 1 protocol has 28 times and 2 protocols were performed.

The results were judged by using the change of HbAlc (Glycated hemoglobin) as the index before the treatment and 12 weeks after the start. Note that any adverse events such as headache, rhinalgia, blood glucose fluctuations and the like were not found in the patients. Also, all of the patients were administered metformin as an internal medicine and performed kinesiology. However, any effects were not observed.

TABLE 12

| No. | Patient | Age | Clinical history (year) | BMI (kg/m$^2$) | Before treatment HbAlc (%) | After 12 wks. HbAlc (%) |
|---|---|---|---|---|---|---|
| 1 | F | 51 | 5 | 32.2 | 8.6 | 6.9 |
| 2 | M | 52 | 6 | 32.3 | 8.23 | 7.0 |
| 3 | M | 60 | 4 | 31.0 | 8.5 | 6.5 |

In all of the patients, HbAlc (%) was decreased compared to those of the treatment start, and the diabetes was improved. From the above, it was demonstrated that SHED-T also has effect for the diabetes.

Example 10

(Treatment Effects of the Culture Sup of SHED-T Against the Refractory Skin Diseases)

SHED-T (2 μg) was dissolved in 5 mL of saline by applying to an affected area of a dog (Labrador retriever, 8 years old, female) with the refractory skin diseases (atopic dermatitis) once a day. 1 cool was 14 times administrations.

Before the use of SHED-T, canine interferon-γ preparation was administered for 2 month, but the treatment effects were not taken. Therefore, the preparation was switched to SHED-T.

Before the start of SHED-T treatment, as shown in FIG. 19A, the affected areas were looked white because hair fallen. After treatment, the hair grew and the affected areas were completely cured beyond recognition that there was the site had dermatitis.

From the above, it was demonstrated that SHED-T has advantageous effects to the refractory skin diseases.

This invention may be embodied in other forms or carried out in other ways without departing from the spirit or essential characteristics thereof. The present disclosure is therefore to be considered as in all aspects illustrate and not restrictive, and all changes which come within the meaning and range of equivalency are intended to be embraced therein.

Various references are cited throughout this specification, each of which is incorporated herein by reference in its entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described the rein can also be used in the practice or testing of the present invention, the preferred methods and materials are now described.

It must be noted that as used herein and in the appended claims, the singular forms "a," "and" and "the" include plural references unless the context clearly dictates otherwise.

What is claimed is:

1. An isolated population of genetically modified STRO-1 positive mammalian stem cells originated from dental pulp and produced by the method comprising:
    isolating a mammalian dental pulp cell from dental pulp tissue;
    performing a primary culture of said mammalian dental pulp cells to obtain primary cultured cells of exfoliated dens deciduous dental pulp stem cells (SHED);
    transducing 4 genes, hTERT, bmi-1, E6, and E7, into said primarily cultured cells of SHED to produce gene-transduced cells SHED (SHED-P); and
    selecting isolated transduced SHED-P,
    wherein the isolated transduced SHED-P are characterized in that: (a) at least 40% of the isolated SHED-P are STRO-1 expression cells having increased neonatal bone quality production relative to non-transduced SHED at the population doubling time of 20, and (b) isolated transduced SHED-P expressing STRO-1 may divide at least 200 times and have telomere repairing ability.

2. The isolated population of genetically modified STRO-1 positive mammalian stem cells according to claim 1, wherein said mammal is selected from the group consisting of human, swine, equine and monkey.

3. The isolated population of genetically modified STRO-1 positive mammalian stem cells according to claim 2, wherein said population of genetically modified STRO-1 positive mammalian stem cells secretes at least IGF-1, VEGF, TGF-$\beta$1 and HGF into a culture supernatant.

* * * * *